US011052065B2

United States Patent
Pinheiro et al.

(10) Patent No.: US 11,052,065 B2
(45) Date of Patent: Jul. 6, 2021

(54) COMPOSITIONS AND METHODS FOR TREATING CANCER WITH A COMBINATION OF PROGRAMMED DEATH RECEPTOR (PD-1) ANTIBODIES AND A CXCR2 ANTAGONIST

(71) Applicant: Merck Sharp & Dohme Corp., Rahway, NJ (US)

(72) Inventors: Elaine M Pinheiro, Needham, MA (US); Michael Rosenzweig, Boston, MA (US); Robert A. Kastelein, Portola Valley, CA (US); David R. Kaufman, Philadelphia, PA (US); Deborah A. Law, Cambridge, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/649,756

(22) PCT Filed: Sep. 24, 2018

(86) PCT No.: PCT/US2018/052335
§ 371 (c)(1),
(2) Date: Mar. 23, 2020

(87) PCT Pub. No.: WO2019/067332
PCT Pub. Date: Apr. 4, 2019

(65) Prior Publication Data
US 2020/0276153 A1    Sep. 3, 2020

Related U.S. Application Data

(60) Provisional application No. 62/564,011, filed on Sep. 27, 2017.

(51) Int. Cl.
*A61K 31/341* (2006.01)
*C07K 16/28* (2006.01)
*A61P 35/04* (2006.01)
*A61K 39/00* (2006.01)

(52) U.S. Cl.
CPC ............ *A61K 31/341* (2013.01); *A61P 35/04* (2018.01); *C07K 16/2818* (2013.01); *A61K 2039/505* (2013.01)

(58) Field of Classification Search
CPC . A61K 31/341; A61K 2039/505; A61P 35/04; C07K 16/2818
USPC ........................................................ 514/471
See application file for complete search history.

(56) References Cited

U.S. PATENT DOCUMENTS

| 7,132,445 B2 | 11/2006 | Taveras et al. |
| 2004/0209946 A1 | 10/2004 | Yin et al. |
| 2011/0160469 A1 | 6/2011 | Fu |
| 2017/0128474 A1 | 5/2017 | Zebala et al. |

FOREIGN PATENT DOCUMENTS

| WO | 2001002369 A2 | 1/2001 |
| WO | 2002010192 A2 | 2/2002 |
| WO | 2002068470 A2 | 9/2002 |
| WO | 2002083624 A1 | 10/2002 |
| WO | 2016079049 A1 | 5/2016 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Ahmadzadeh et al., Tumor antigen-specific CD8 T cells infiltrating the tumor express high levels of PD-1 and are functionally impaired, Blood, 2009, 1537-1544, 114.
Brahmer et al., Safety and Activity of Anti-PD-L1 Antibody in Patients with Advanced Cancer, The New England Journal of Medicine, 2012, pp. 2455-2465, vol. 366, No. 26.
Budhu, Sadna, The importance of animal models in tumor immunity and immunotherapy, Curr Opin Genet Dev, 2014, 46-51, 24.
David, Justin M. et al., The IL-8/IL-8R Axis: A Double Agent in Tumor Immune Resistance, Vaccines, 2016, 1-15, 4(22).

(Continued)

*Primary Examiner* — Kristin A Vajda
(74) *Attorney, Agent, or Firm* — Eric A. Meade; John C. Todaro

(57) ABSTRACT

The present invention relates to methods of treating a cell proliferation disorder (e.g., cancer) comprising administering: (a) a compound having the Formula (I), wherein $R^1$ or $R^2$ are as herein defined, or a pharmaceutically acceptable salt thereof; and (b) an anti-human PD-1 antibody or antigen binding fragment thereof to a human patient in need thereof. Also disclosed are therapeutic combinations and kits containing such agents for the treatment of cancers.

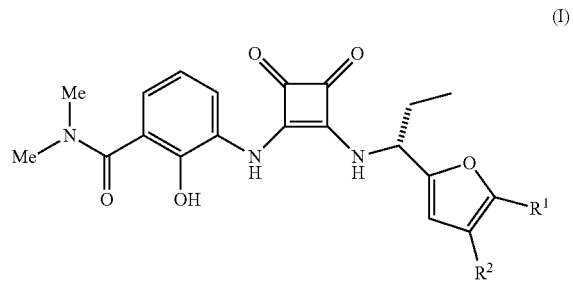

(I)

11 Claims, 3 Drawing Sheets

Specification includes a Sequence Listing.

(56) References Cited

OTHER PUBLICATIONS

Dong et al., Tumor-associated B7-H1 promotes T-cell apoptosis: A potential mechanism of immune evasion, Nature Medicine, 2002, pp. 793-800, vol. 8(8).
Dwyer, Michael P. et al., Discovery of 2-Hydroxy-N,N-dimethyl-3-{2-[[(R)-1-(5-methylfuran-2-yl)propyl]amino]-3,4-dioxocyclobut-1-enylamino}benzamide (SCH 527123): A Potent, Orally Bioavailable CXCR2/CXCR1 Receptor Antagonist, J. Med. Chem., 2006, 7603-9606, 49(26).
Gao et al., Overexpression of PD-L1 Significantly Associates with Tumor Aggressiveness and Postoperative Recurrence in Human Hepatocellular Carcinoma, Clinical Cancer Research, 2009, 971-979, 15.
Garon et al., Pembrolizumab for the Treatment of Non-Small-Cell Lung Cancer, The New England Journal of Medicine, 2015, pp. 2018-2028, vol. 372, No. 21.
Gentles, Andrew J. et al., The prognostic landscape of genes and infiltrating immune cells across human cancers, Nature Medicine, 2015, 938-945, 21(8).
Ghebeh et al., FOXP3+ Tregs and B7-H1+/PD-1+T lymphocytes co-infiltrate the tumor tissues of high-risk breast cancer patients: Implication for immunotherapy, BMC Cancer, 2008, 57-68, 8.
Ghebeh et al., The B7-H1 (PD-L1) T Lymphocyte-Inhibitory Molecule Is Expressed in Breast Cancer Patients with Infiltrating Ductal Carcinoma: Correlation with Important High-Risk Prognostic Factors, Neoplasia, 2006, 190-198, 8.
Hamanishi et al., Programmed cell death 1 ligand 1 and tumor-infiltrating CD8+ T lymphocytes are prognostic factors of human ovarian cancer, Proceedings of the National Academy of Sciences USA, 2007, 3360-3365, 104.
Hamid et al., Safety and Tumor Responses with Lambrolizumab (Anti-PD-1) in Melanoma, New Eng. J. Med., 2013, 134-144, 369(2).
Herold, Anti-CD3 Monoclonal Antibody in New-Onset Type 1 Diabetes Mellitus, New England Journal of Medicine, 2002, pp. 1692-1698, 346.
Hino et al., Tumor cell expression of programmed cell death-1 ligand 1 is a prognostic factor for malignant melanoma, Cancer, 2010, 1757-1766, 116(7).
Hu-Lieskovan, Siwen, Improved antitumor activity of immunotherapy with BRAF and MEK inhibitors in BRAFV600E melanoma, Sci Transl Med, 2015, 1-21, 7(279): 279ra41.
Inman et al., PD-L1 (B7-H1) expression by urothelial carcinoma of the bladder and BCG-induced granulomata: associations with localized stage progression, Cancer, 2007, 1499-1505, 109.
Jiang, Y., T-cell exhaustion in the tumor microenvironment, Cell Death and Disease, 2015, 1-9, 6, e1792.
Li, Li et al., CXCR2—CXCL1 axis is correlated with neutrophil infiltration and predicts a poor prognosis in hepatocellular carcinoma, Journal of Experimental & Clinical Cancer Research, 2015, 1-10, 34:129.
Liu et al., Randomised, double blind, placebo controlled study of interferon b-1a in relapsing-remitting multiple sclerosis analysed by area under disability/time curves, N. Neurol. Neurosurg. Psych., 1999, pp. 451-456, 67.
Nakanishi et al., Overexpression of B7-H1 (PD-L1) significantly associates with tumor grade and postoperative prognosis in human urothelial cancers, Cancer Immunol. Immunother., 2007, 1173-1182, 56.

Nomi et al., Clinical Significance and Therapeutic Potential of the Programmed Death-1 Ligand/Programmed Death-1 Pathway in Human Pancreatic Cancer, Clinical Cancer Research, 2007, pp. 2151-2157, vol. 13.
Ohigashi et al., Clinical Significance of Programmed Death-1 Ligand-1 and Programmed Death-1 Ligand-2 Expression in Human Esophageal Cancer, Clin. Cancer Research, 2005, 2947-2953, 11.
Pham, Christina D., Differential Immune Microenvironments and Response to Immune Checkpoint Blockade among Molecular Subtypes of Murine Medulloblastoma, Clinical Cancer Research, 2016, 582-595, 22(3).
Portielje, IL-12: a promising adjuvant for cancer vaccination, Cancer Immunol Immunother, 2003, 133-144, 52.
Robert et al., Anti-programmed-death-receptor-1 treatment with pembrolizumab in ipilimumab-refractory advanced melanoma: a randomised dose-comparison cohort of a phase 1 trial, The Lancet, 2014, pp. 1109-1117, vol. 384.
Robert et al., Nivolumab in Previously Untreated Melanoma without BRAF Mutation, The New England Journal of Medicine, 2015, pp. 320-330, vol. 372, No. 4.
Robert et al., Pembrolizumab versus Ipilimumab in Advanced Melanoma, The New England Journal of Medicine, Jun. 25, 2015, pp. 2521-2532, 372.
Saintigny, Pierre et al., CXCR2Expression in TumorCells is a Poor Prognostic Factor and Promotes Invasion and Metastasis in Lung Adenocarcinoma, Cancer Research, 2013, 571-582, 73.
Sanmamed, M. F. et al., Changes in serum interleukin-8 (IL-8) levels reflect and predict response to anti-PD-1 treatment in melanoma and non-small-cell lung cancer patients, Annals of Oncology, 2017, 1988-1995, 28.
Shimauchi et al., Augmented expression of programmed death-1 in both neoplastic and non-neoplastic CD4+ cells in adult T-cell leukemia/lymphoma, Int. J. Cancer, 2007, 2585-2590, 121.
Steele, Colin W. et al., CXCR2 Inhibition Profoundly Suppresses Metastases and Augments Immunotherapy in Pancreatic Ductal Adenocarcinoma, Cancer Cell, 2016, 832-845, 29(6).
Steele, Colin W. et al., CXCR2 inhibition suppresses acute and chronic pancreatic inflammation, Journal of Pathology, 2015, 85-97, 237.
Thompson et al., PD-1 Is Expressed by Tumor-Infiltrating Immune Cells and is Associated with Poor Outcome for Patients with Renal Cell Carcinoma, Clinical Cancer Research, 2007, pp. 1757-1761, vol. 15.
Thompson et al., Significance of B7-H1 Overexpression in Kidney Cancer, Cancer, 2006, 206-211, 5.
Topalian et al., Safety, Activity, and Immune Correlates of Anti-PD-1 Antibody in Cancer, New Eng. J. Med., 2012, 2443-2454, 366(26).
Topalian et al., Survival, Durable Tumor Remission, and Long-Term Safety in Patients With Advanced Melanoma Receiving Nivolumab, Clinical Journal of Oncology, 2014, pp. 1020-1030, vol. 32, No. 10.
Wolchok et al., Nivolumab plus Ipilimumab in Advanced Melanoma, The New England Journal of Medicine, 2013, pp. 122-133, vol. 369(2).
Yang et al., A Randomized Trial of Bevacizumab, an Anti-Vascular Endothelial Growth Factor Antibody, for Metastatic Renal Cancer, New England Journal of Medicine, 2003, pp. 427-434, 349.
Yang et al., PD-L1: PD-1 Interaction Contributes to the Functional Suppression of T-Cell Responses to Human Uveal Melanoma Cells In Vitro, Invest Ophthalmol Vis Sci, 2008, 2518-2525, 49(6).

* cited by examiner

- ■ Isotype Cntrl + Vehicle
- ◇ Anti-PD-1 + Vehicle
- ● Isotype Cntrl + Navarixin (bid)
- ▲ Anti-PD-1 + Navarixin (bid)
- ▽ Anti-PD-1 + Navarixin (qd)

- ■ Isotype Cntrl + Vehicle
- ◇ Anti-PD-1 + Vehicle
- ● Isotype Cntrl + Navarixin (bid)
- ▲ Anti-PD-1 + Navarixin (bid)
- ▽ Anti-PD-1 + Navarixin (qd)

SEQUENCE LISTING

```
<160> NUMBER OF SEQ ID NOS: 21

<210> SEQ ID NO 1
<211> LENGTH: 15
<212> TYPE: PRT
<213> ORGANISM: Artificial Sequence
<220> FEATURE:
<223> OTHER INFORMATION: Pembrolizumab, light chain CDR1

<400> SEQUENCE: 1

Arg Ala Ser Lys Gly Val Ser Thr Ser Gly Tyr Ser Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Pembrolizumab, light chain CDR2

<400> SEQUENCE: 2

Leu Ala Ser Tyr Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Pembrolizumab, light chain CDR3

<400> SEQUENCE: 3
```

```
Gln His Ser Arg Asp Leu Pro Leu Thr
1               5

<210> SEQ ID NO 4
<211> LENGTH: 111
<212> TYPE: PRT
<213> ORGANISM: Artificial Sequence
<220> FEATURE:
<223> OTHER INFORMATION: Pembrolizumab, variable region light chain

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 5
<211> LENGTH: 218
<212> TYPE: PRT
<213> ORGANISM: Artificial Sequence
<220> FEATURE:
<223> OTHER INFORMATION: Pembrolizumab, light chain

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

```
His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 6
<211> LENGTH: 5
<212> TYPE: PRT
<213> ORGANISM: Artificial Sequence
<220> FEATURE:
<223> OTHER INFORMATION: Pembrolizumab, heavy chain CDR1

<400> SEQUENCE: 6

Asn Tyr Tyr Met Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Pembrolizumab, heavy chain CDR2

<400> SEQUENCE: 7

Gly Ile Asn Pro Ser Asn Gly Gly Thr Asn Phe Asn Glu Lys Phe Lys
1               5                   10                  15

Asn

<210> SEQ ID NO 8
<211> LENGTH: 11
<212> TYPE: PRT
<213> ORGANISM: Artificial Sequence
<220> FEATURE:
<223> OTHER INFORMATION: Pembrolizumab, heavy chain CDR3

<400> SEQUENCE: 8

Arg Asp Tyr Arg Phe Asp Met Gly Phe Asp Tyr
1               5                   10

<210> SEQ ID NO 9
<211> LENGTH: 120
<212> TYPE: PRT
<213> ORGANISM: Artificial Sequence
<220> FEATURE:
<223> OTHER INFORMATION: Pembrolizumab, heavy chain variable region

<400> SEQUENCE: 9

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110
```

```
Gly Thr Thr Val Thr Val Ser Ser
        115                 120
```

<210> SEQ ID NO 10
<211> LENGTH: 447
<212> TYPE: PRT
<213> ORGANISM: Artificial Sequence
<220> FEATURE:
<223> OTHER INFORMATION: Pembrolizumab, heavy chain

<400> SEQUENCE: 10

```
Gln Val Gln Leu Val Gln Ser Gly Val Glu Val Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Gln Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 11
<211> LENGTH: 11
<212> TYPE: PRT
<213> ORGANISM: Artificial Sequence
<220> FEATURE:
<223> OTHER INFORMATION: Nivolumab, light chain CDR1

<400> SEQUENCE: 11

Arg Ala Ser Gln Ser Val Ser Ser Tyr Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Nivolumab, light chain CDR2

<400> SEQUENCE: 12

Asp Ala Ser Asn Arg Ala Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Nivolumab, light chain CDR3

<400> SEQUENCE: 13

Gln Gln Ser Ser Asn Trp Pro Arg Thr
1               5

<210> SEQ ID NO 14
<211> LENGTH: 107
<212> TYPE: PRT
<213> ORGANISM: Artificial Sequence
<220> FEATURE:
<223> OTHER INFORMATION: Nivolumab, light chain variable region

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
            100                 105

<210> SEQ ID NO 15
<211> LENGTH: 214
<212> TYPE: PRT
<213> ORGANISM: Artificial Sequence
<220> FEATURE:
<223> OTHER INFORMATION: Nivolumab, light chain

<400> SEQUENCE: 15

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 16
<211> LENGTH: 5
<212> TYPE: PRT
<213> ORGANISM: Artificial Sequence
<220> FEATURE:
<223> OTHER INFORMATION: Nivolumab, heavy chain CDR1

<400> SEQUENCE: 16

Asn Ser Gly Met His
 1               5

<210> SEQ ID NO 17
<211> LENGTH: 17
<212> TYPE: PRT
<213> ORGANISM: Artificial Sequence
```

<220> FEATURE:
<223> OTHER INFORMATION: Nivolumab, heavy chain CDR2

<400> SEQUENCE: 17

Val Ile Trp Tyr Asp Gly Ser Lys Arg Tyr Tyr Ala Asp Ser Val Lys
1               5                   10                  15
Gly

<210> SEQ ID NO 18
<211> LENGTH: 4
<212> TYPE: PRT
<213> ORGANISM: Artificial Sequence
<220> FEATURE:
<223> OTHER INFORMATION: Nivolumab, heavy chain CDR3

<400> SEQUENCE: 18

Asn Asp Asp Tyr
1

<210> SEQ ID NO 19
<211> LENGTH: 113
<212> TYPE: PRT
<213> ORGANISM: Artificial Sequence
<220> FEATURE:
<223> OTHER INFORMATION: Nivolumab, heavy chain variable region

<400> SEQUENCE: 19

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 20
<211> LENGTH: 440
<212> TYPE: PRT
<213> ORGANISM: Artificial Sequence
<220> FEATURE:
<223> OTHER INFORMATION: Nivolumab, heavy chain

<400> SEQUENCE: 20

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe

```
                65                  70                  75                  80
        Leu Gln Met Asn Ser Leu Arg Ala Glu Asp Thr Ala Val Tyr Tyr Cys
                        85                  90                  95

Ala Thr Asn Asp Asp Tyr Trp Gly Gln Gly Thr Leu Val Thr Val Ser
                        100                 105                 110

Ser Ala Ser Thr Lys Gly Pro Ser Val Phe Pro Leu Ala Pro Cys Ser
                        115                 120                 125

Arg Ser Thr Ser Glu Ser Thr Ala Ala Leu Gly Cys Leu Val Lys Asp
                    130                 135                 140

Tyr Phe Pro Glu Pro Val Thr Val Ser Trp Asn Ser Gly Ala Leu Thr
        145                 150                 155                 160

Ser Gly Val His Thr Phe Pro Ala Val Leu Gln Ser Ser Gly Leu Tyr
                            165                 170                 175

Ser Leu Ser Ser Val Val Thr Val Pro Ser Ser Ser Leu Gly Thr Lys
                        180                 185                 190

Thr Tyr Thr Cys Asn Val Asp His Lys Pro Ser Asn Thr Lys Val Asp
                        195                 200                 205

Lys Arg Val Glu Ser Lys Tyr Gly Pro Pro Cys Pro Pro Cys Pro Ala
                    210                 215                 220

Pro Glu Phe Leu Gly Gly Pro Ser Val Phe Leu Phe Pro Pro Lys Pro
        225                 230                 235                 240

Lys Asp Thr Leu Met Ile Ser Arg Thr Pro Glu Val Thr Cys Val Val
                            245                 250                 255

Val Asp Val Ser Gln Glu Asp Pro Glu Val Gln Phe Asn Trp Tyr Val
                        260                 265                 270

Asp Gly Val Glu Val His Asn Ala Lys Thr Lys Pro Arg Glu Glu Gln
                        275                 280                 285

Phe Asn Ser Thr Tyr Arg Val Val Ser Val Leu Thr Val Leu His Gln
                        290                 295                 300

Asp Trp Leu Asn Gly Lys Glu Tyr Lys Cys Lys Val Ser Asn Lys Gly
        305                 310                 315                 320

Leu Pro Ser Ser Ile Glu Lys Thr Ile Ser Lys Ala Lys Gly Gln Pro
                            325                 330                 335

Arg Glu Pro Gln Val Tyr Thr Leu Pro Pro Ser Gln Glu Glu Met Thr
                        340                 345                 350

Lys Asn Gln Val Ser Leu Thr Cys Leu Val Lys Gly Phe Tyr Pro Ser
                        355                 360                 365

Asp Ile Ala Val Glu Trp Glu Ser Asn Gly Gln Pro Glu Asn Asn Tyr
                    370                 375                 380

Lys Thr Thr Pro Pro Val Leu Asp Ser Asp Gly Ser Phe Phe Leu Tyr
        385                 390                 395                 400

Ser Arg Leu Thr Val Asp Lys Ser Arg Trp Gln Glu Gly Asn Val Phe
                            405                 410                 415

Ser Cys Ser Val Met His Glu Ala Leu His Asn His Tyr Thr Gln Lys
                        420                 425                 430

Ser Leu Ser Leu Ser Leu Gly Lys
                    435                 440

<210> SEQ ID NO 21
<211> LENGTH: 290
<212> TYPE: PRT
<213> ORGANISM: Homo sapiens

<400> SEQUENCE: 21
```

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
                35                  40                  45

Asp Leu Ala Ala Leu Ile Val Tyr Trp Glu Met Glu Asp Lys Asn Ile
            50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
                115                 120                 125

Lys Val Asn Ala Pro Tyr Asn Lys Ile Asn Gln Arg Ile Leu Val Val
                130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
                210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
290
```

COMPOSITIONS AND METHODS FOR TREATING CANCER WITH A COMBINATION OF PROGRAMMED DEATH RECEPTOR (PD-1) ANTIBODIES AND A CXCR2 ANTAGONIST

CROSS-REFERENCE

This application is a U.S. National Phase application of PCT/US2018/052335, filed Sep. 24, 2018, which claims the benefit of U.S. Provisional Application No. 62/564,011, filed Sep. 27, 2017.

FIELD OF THE INVENTION

The present invention relates to combination therapies useful for the treatment of of a cell proliferation disorder, such as cancer. In particular, the invention relates to a combination therapy which comprises an antibody that binds to a Programmed Death 1 protein (PD-1) or an antigen binding fragment thereof, and a CXCR2 antagonist.

BACKGROUND OF THE INVENTION

PD-1 is recognized as an important player in immune regulation and the maintenance of peripheral tolerance. PD-1 is moderately expressed on naive T, B and NKT cells and up-regulated by T/B cell receptor signaling on lymphocytes, monocytes and myeloid cells (Sharpe et al., The function of programmed cell death 1 and its ligands in regulating autoimmunity and infection. *Nature Immunology* (2007); 8:239-245).

Two known ligands for PD-1, PD-L1 (B7-H1) and PD-L2 (B7-DC), are expressed in human cancers arising in various tissues. In large sample sets of e.g., ovarian, renal, colorectal, pancreatic, liver cancers and melanoma, it was shown that PD-L1 expression correlated with poor prognosis and reduced overall survival irrespective of subsequent treatment (Dong et al., *Nat Med.* 8(8):793-800 (2002); Yang et al. *Invest Ophthalmol Vis Sci.* 49: 2518-2525 (2008); Ghebeh et al. *Neoplasia* 8:190-198 (2006); Hamanishi et al., *Proc. Natl. Acad. Sci. USA* 104: 3360-3365 (2007); Thompson et al., *Cancer* 5: 206-211 (2006); Nomi et al., *Clin. Cancer Research* 13:2151-2157 (2007); Ohigashi et al., *Clin. Cancer Research* 11: 2947-2953; Inman et al., *Cancer* 109: 1499-1505 (2007); Shimauchi et al. *Int. J Cancer* 121:2585-2590 (2007); Gao et al. *Clin. Cancer Research* 15: 971-979 (2009); Nakanishi *J. Cancer Immunol Immunother.* 56: 1173-1182 (2007); and Hino et al., *Cancer* 00: 1-9 (2010)).

Similarly, PD-1 expression on tumor infiltrating lymphocytes was found to mark dysfunctional T cells in breast cancer and melanoma (Ghebeh et al, *BMC Cancer.* 2008 8:5714-15 (2008); Ahmadzadeh et al., *Blood* 114: 1537-1544 (2009)) and to correlate with poor prognosis in renal cancer (Thompson et al., *Clinical Cancer Research* 15: 1757-1761(2007)). Thus, it has been proposed that PD-L1 expressing tumor cells interact with PD-1 expressing T cells to attenuate T cell activation and evasion of immune surveillance, thereby contributing to an impaired immune response against the tumor.

Immune checkpoint therapies targeting the PD-1 axis have resulted in groundbreaking improvements in clinical response in multiple human cancers (Brahmer et al., *N Engl J Med* 2012, 366: 2455-65; Garon et al. *N Engl J Med* 2015, 372: 2018-28; Hamid et al., *N Engl J Med* 2013, 369: 134-44; Robert et al., *Lancet* 2014, 384: 1109-17; Robert et al *N Engl J Med* 2015, 372: 2521-32; Robert et al., *N Engl J Med* 2015, 372: 320-30; Topalian et al., *N Engl J Med* 2012, 366: 2443-54; Topalian et al., *J Clin Oncol* 2014, 32: 1020-30; Wolchok et al., *N Engl J Med* 2013, 369: 122-33). Immune therapies targeting the PD-1 axis include monoclonal antibodies directed to the PD-1 receptor (KEYTRUDA™ (pembrolizumab), Merck and Co., Inc., Kenilworth, N.J., USA and OPDIVO™ (nivolumab), Bristol-Myers Squibb Company, Princeton, N.J., USA) and also those that bind to the PD-L1 ligand (MPDL3280A; TECENTRIQ™ (atezolizumab), Genentech, San Francisco, Calif., USA). Both therapeutic approaches have demonstrated antitumor effects in numerous cancer types.

It has been proposed that the efficacy of such antibodies might be enhanced if administered in combination with other approved or experimental cancer therapies, e.g., radiation, surgery, chemotherapeutic agents, targeted therapies, agents that inhibit other signaling pathways that are disregulated in tumors, and other immune enhancing agents. One such signaling pathway involves ELRCXC chemokines, which bind to the CXC G protein-coupled receptors, CXCR2 and CXCR1. The CXCR2 receptor is highly expressed across tumor types and has been shown to significantly correlate with poor survival (Steele, C. W. et al., 2016, *Cancer Cell* 29:832; Saintigny, P. et al., 2013, *Cancer Res.*, 73:571. Li, L. et al., 2015, *J. Exp. Clin. Cancer Res.* 34:129).

The CXCR2 receptor is also highly expressed on human myeloid-derived suppressor cells (MDSCs) and plays a role in the homing of MDSCs in the tumor microenvironment (TME). MDSCs are an adverse cancer-wide prognostic population of immune infiltrating cells. MDSCs contribute to tumor immune evasion through a variety of mechanisms that suppress local T-cell activation and viability (Gentles et al., 2015, *Nature Med.* 21:938). MDSCs can also influence tumor progression by promoting tumor metastases, angiogenesis and tumor cell invasion.

The CXCR2 and CXCR1 receptors differ in their chemokine-binding specificity. CXCR1 and CXCR2 can bind CXCL8 (IL-8) and CXCL6. CXCL5, CXCL1, CXCL2, CXCL3, CXCL7 can also bind and activate CXCR2 in humans. In addition to promoting tumor resistance by enhancing the immunosuppressive TME through MDSC recruitment, reports have shown that the ELRCXC chemokine-CXCR1/2 axis can promote angiogenic responses and activate epithelial-mesynchymal transition (EMT) differentiation programs which are associated with its role in metastasis and stemness (David, J. M. et al., 2016, *Vaccines* 4:1).

SUMMARY OF THE INVENTION

In a first aspect, the invention provides a method of treating a cell proliferation disorder, e.g., cancer, comprising administering:

(a) a compound having the Formula I

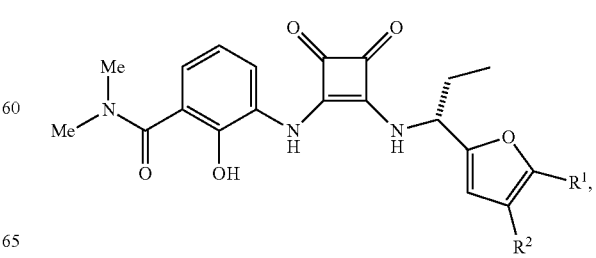

wherein $R^1$ are $R^2$ are independently H or $C_1$-$C_5$ alkyl or a pharmaceutically acceptable salt thereof; and (b) an anti-human PD-1 antibody or antigen binding fragment thereof to a human patient in need thereof.

In one embodiment of this method (embodiment no. 1), the cell proliferation disorder is cancer, wherein the cancer is prostate cancer, pancreatic cancer, melanoma, non-small cell lung cancer, head and neck cancer, urothelial cancer, breast cancer, gastrointestinal cancer, multiple myeloma, hepatocellular cancer, non-Hodgkin lymphoma, renal cancer, Hodgkin lymphoma, mesothelioma, microsatellite instability-high cancer, mismatch repair deficient cancer, ovarian cancer, small cell lung cancer, esophageal cancer, anal cancer, biliary tract cancer, colorectal cancer, cervical cancer, thyroid cancer, or salivary cancer. Also, in some embodiments above method, the cancer expresses an elevated level of PD-L1, such as cancers having tumors with a tumor proportion score (TPS) of ≥1%, ≥10% or ≥50%. For example, the level of PD-L1 TPS is determined by an FDA-approved test.

In embodiment no. 2 of this method, the cancer is prostate cancer. For instance, the prostate cancer can be metastatic castrate-resistant prostate cancer.

In embodiment no. 3 of this method, the cancer is pancreatic cancer. For instance, the pancreatic cancer is pancreatic ductal adenocarcinoma.

In embodiment no. 4 of this method, the compound of Formula I is

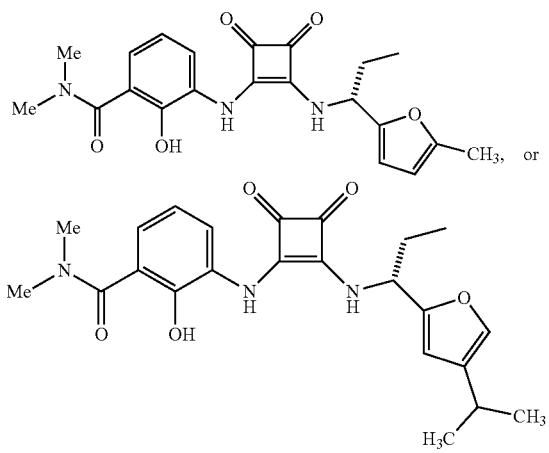

or a pharmaceutically acceptable salt thereof.

In embodiment no. 5 of this method, the compound of Formula I is

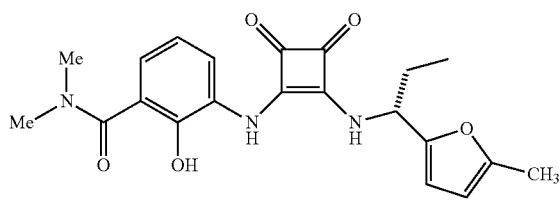 [SMILES: CC[C@@H](Nc1c(Nc2cccc(C(=O)N(C)C)c2O)c(=O)c1=O)c1ccc(C)o1]

(known as "navarixin") or a pharmaceutically acceptable salt thereof.

In embodiment no. 6 of this method, the compound of Formula I is

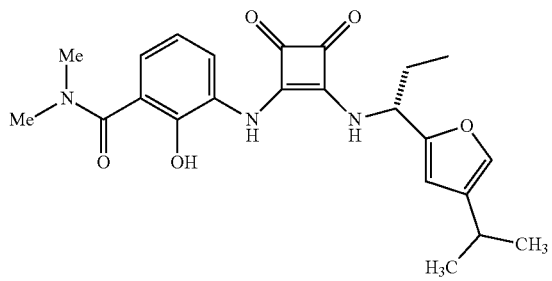 [SMILES: CC[C@@H](Nc1c(Nc2cccc(C(=O)N(C)C)c2O)c(=O)c1=O)c1cc(C(C)C)co1]

or a pharmaceutically acceptable salt thereof.

In embodiment no. 6 of this method, the human patient is administered:

(a) 200 mg or 240 mg of the anti-human PD-1 antibody or antigen binding fragment thereof and from 5 to 200 mg of the compound of Formula I or a pharmaceutically acceptable salt thereof; or (b) 2 mg/kg of an anti-human PD-1 antibody or antigen binding fragment thereof and from 5 to 200 mg of the compound of Formula I or a pharmaceutically acceptable salt thereof, wherein the anti-human PD-1 antibody or antigen binding fragment thereof is administered once every three weeks and the compound of Formula I or a pharmaceutically acceptable salt thereof is administered once daily or twice daily.

In a second aspect, the invention provides a kit comprising:

(a) a compound having the Formula I

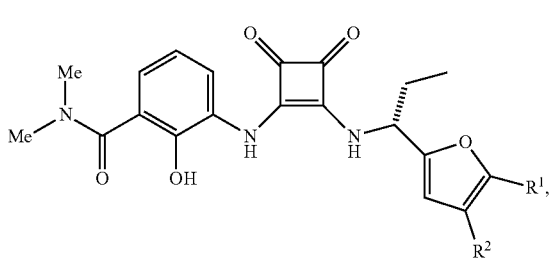

wherein $R^1$ are $R^2$ are independently H or $C_1$-$C_5$ alkyl or a pharmaceutically acceptable salt thereof; and (b) an anti-human PD-1 antibody or antigen binding fragment thereof.

In embodiment no. 1 of this kit, the kit further comprises instructions for administering the compound of Formula I and the anti-human PD-1 antibody or antigen binding fragment thereof to a human patient.

In a third aspect, the invention provides a therapeutic combination, comprising:
(a) a compound having the Formula I

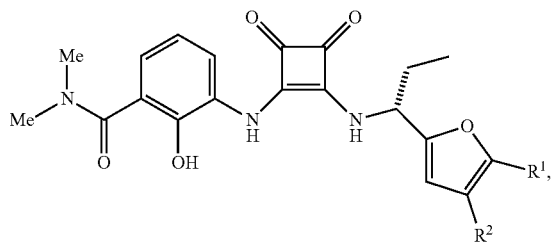

I wherein $R^1$ are $R^2$ are independently H or $C_1$-$C_5$ alkyl or a pharmaceutically acceptable salt thereof; and
(b) an anti-human PD-1 antibody or antigen binding fragment thereof for treating a cell proliferation disorder, e.g., cancer, in a human patient.

In certain embodiments of the first, second, or third aspects, the anti-human PD-1 antibody or antigen binding fragment thereof comprises three light chain CDRs of SEQ ID NO:1, SEQ ID NO:2 and SEQ ID NO:3 and three heavy chain CDRs of SEQ ID NO:6, SEQ ID NO:7 and SEQ ID NO:8.

In certain embodiments of the first, second, or third aspects, the anti-human PD-1 antibody or antigen binding fragment thereof comprises a $V_L$ region which comprises the amino acid sequence set forth in SEQ ID NO:4, and a $V_H$ region which comprises the amino acid sequence set forth in SEQ ID NO:9.

In certain embodiments of the first, second, or third aspects, the anti-human PD-1 antibody or antigen binding fragment thereof comprises a light chain comprising or consisting of a sequence of amino acids as set forth in SEQ ID NO:5 and a heavy chain comprising or consisting of a sequence of amino acids as set forth in SEQ ID NO:10.

In certain embodiments of the first, second, or third aspects, the anti-human PD-1 antibody or antigen binding fragment thereof is pembrolizumab.

In certain embodiments of the first, second, or third aspects, the anti-human PD-1 antibody or antigen binding fragment thereof is nivolumab.

DETAILED DESCRIPTION OF THE INVENTION

Figure 1:
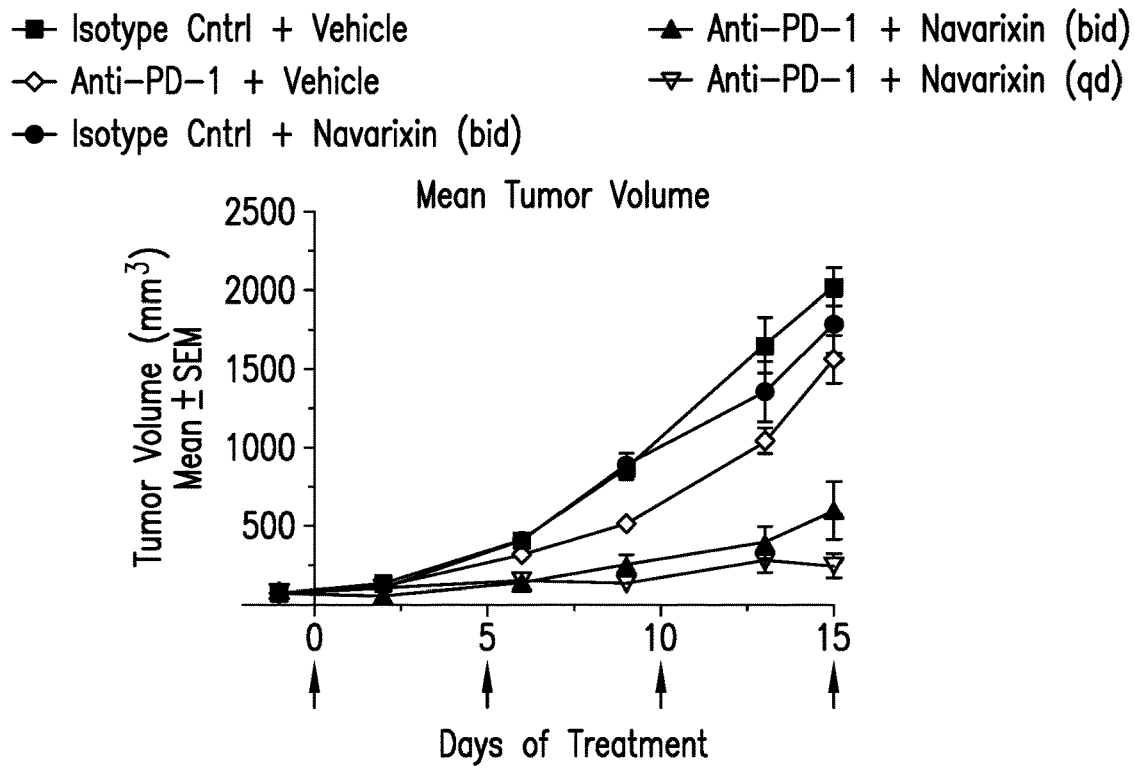
FIG. 1 shows the mean tumor volume vs. days of treatment in five treatment groups of tumor-bearing mice in a B16-F10 melanoma model.
Figure 2:
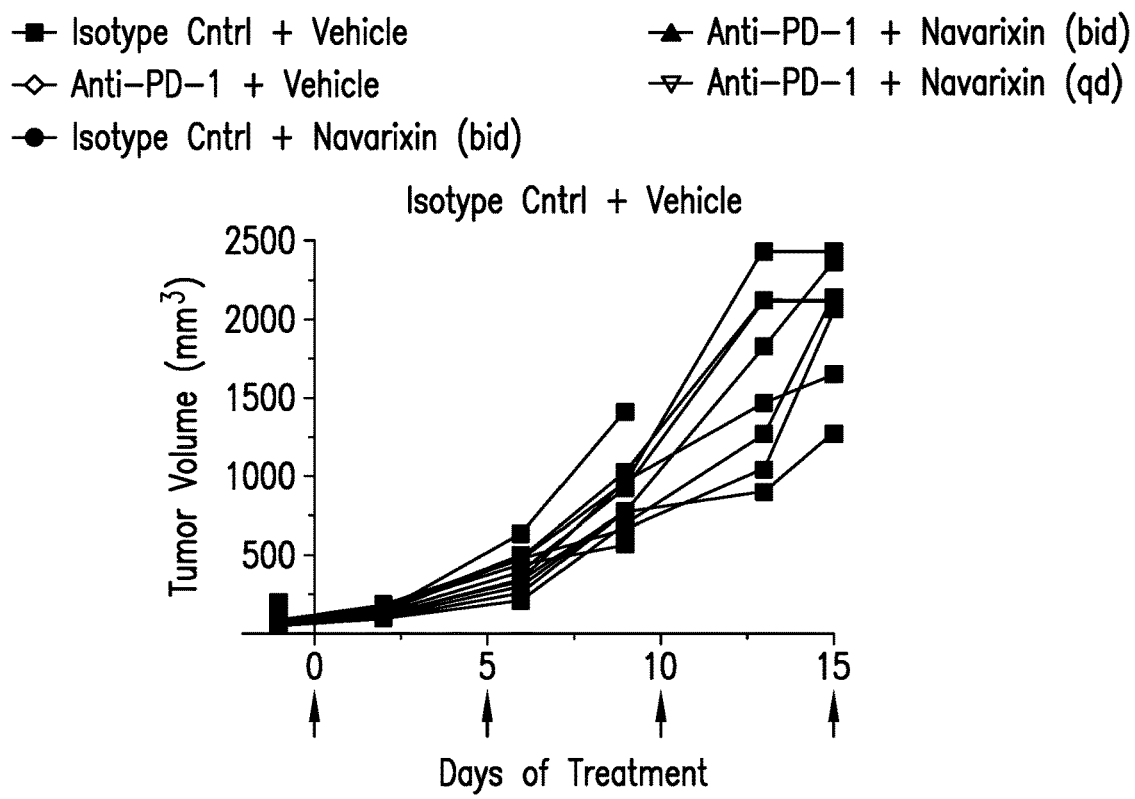
FIG. 2 shows the tumor volume vs. days of treatment in the isotype control (control IgG mouse monoclonal antibody) treatment group.

Abbreviations
μg, ug Microgram
BID One dose twice daily
C57Bl/6 Common inbred strain of laboratory mouse, also "C57 black 6", "C57", "black 6", or "B6"
CDR Complementary determining region
CR Complete regression
Ctrl Control
DFS Disease free survival
DLT Dose limiting toxicity
FFPE Formalin-fixed, paraffin-embedded
FR Framework region
IgG Immunoglobulin G
IgG1 Immunoglobulin G subclass 1
IHC Immunohistochemistry or immunohistochemical
IP Intraperitoneal
IT Intratumoral
kg Kilogram
mAb Monoclonal antibody
mg Milligram
mIgG1 Murine immunoglobulin G subclass 1, Isotype control mAb for anti-PD-1 antibody muDX400
mL Milliliter
mm Millimeter
$mm^3$ Cubic millimeter, 0.001 mL
MPK Milligram per kilogram
MTD Maximum tolerated dose
n Number of subjects in a treatment group
NCI National Cancer Institute
OR Overall response
OS Overall survival
PBS Phosphate-buffered saline, vehicle control for CXCR2 antagonists
PD-1 Programmed cell death protein 1
PFS Progression free survival
PR Partial response
p-values Calculated probability
QD One dose per day
RECIST Response Evaluation Criteria in Solid Tumors
SD Stable disease
SEM Standard error of the mean
TGI Tumor growth inhibition
T/C Median tumor volume of the treated animal/Median tumor volume of the control animal
$V_H$ immunoglobulin heavy chain variable region
$V_K$ immunoglobulin kappa light chain variable region
$V_L$ immunoglobulin light chain variable region
Additional abbreviations may be defined throughout this disclosure.

Definitions

Certain technical and scientific terms are specifically defined below. Unless specifically defined elsewhere in this document, all other technical and scientific terms used herein have the meaning commonly understood by one of ordinary skill in the art to which this disclosure relates.

"About" when used to modify a numerically defined parameter (e.g., the dose of an anti-PD-1 antibody, or antigen binding fragment thereof, or CXCR2 antagonist, or the length of treatment time with a combination therapy described herein) means that the parameter may vary by as much as 10% below or above the stated numerical value for that parameter; where appropriate, the stated parameter may be rounded to the nearest whole number. For example, a dose of about 5 mg/kg may vary between 4.5 mg/kg and 5.5 mg/kg.

As used herein, including the appended claims, the singular forms of words such as "a," "an," and "the," include their corresponding plural references unless the context clearly dictates otherwise.

The terms "administration of" and or "administering" a compound should be understood to include providing a compound described herein, or a pharmaceutically acceptable salt thereof, and compositions of the foregoing to a subject.

The term "alkyl" refers to a monovalent straight or branched chain, saturated aliphatic hydrocarbon radical having a number of carbon atoms in the specified range. Thus, for example, "$C_1$-$C_5$ alkyl" refers to any of pentyl alkyl isomers as well as n-, iso-, sec-, and tert-butyl, n- and iso-propyl, ethyl, and methyl.

As used herein, the term "antibody" refers to any form of immunoglobulin molecule that exhibits the desired biological or binding activity. Thus, it is used in the broadest sense and specifically covers, but is not limited to, monoclonal antibodies (including full length monoclonal antibodies), polyclonal antibodies, multi specific antibodies (e.g., bispecific antibodies), humanized, fully human antibodies, and chimeric antibodies. "Parental antibodies" are antibodies obtained by exposure of an immune system to an antigen prior to modification of the antibodies for an intended use, such as humanization of an antibody for use as a human therapeutic. As used herein, the term "antibody" encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The variable regions of each light/heavy chain pair form the antibody binding site. Thus, in general, an intact antibody has two binding sites. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

As used herein, unless otherwise indicated, "antibody fragment" or "antigen binding fragment" refers to a fragment of an antibody that retains the ability to bind specifically to the antigen, e.g., fragments that retain one or more CDR regions. An antibody that "specifically binds to" PD-1 or PD-L1 is an antibody that exhibits preferential binding to PD-1 or PD-L1 (as appropriate) as compared to other proteins, but this specificity does not require absolute binding specificity. An antibody is considered "specific" for its intended target if its binding is determinative of the presence of the target protein in a sample, e.g., without producing undesired results such as false positives. Antibodies, or binding fragments thereof, will bind to the target protein with an affinity that is at least two fold greater, preferably at least ten times greater, more preferably at least 20-times greater, and most preferably at least 100-times greater than the affinity with non-target proteins.

Antigen binding portions include, for example, Fab, Fab', F(ab')2, Fd, Fv, fragments including complementarity determining regions (CDRs), and single chain variable fragment antibodies (scFv), and polypeptides that contain at least a portion of an immunoglobulin that is sufficient to confer specific antigen binding to the PD-1 or PD-L1. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

As used herein, the terms "at least one" item or "one or more" item each include a single item selected from the list as well as mixtures of two or more items selected from the list.

As used herein, the term "immune response" relates to any one or more of the following: specific immune response, non-specific immune response, both specific and non-specific response, innate response, primary immune response, adaptive immunity, secondary immune response, memory immune response, immune cell activation, immune cell-proliferation, immune cell differentiation, and cytokine expression.

The term "pharmaceutically acceptable carrier" refers to any inactive substance that is suitable for use in a formulation for the delivery of a therapeutic agent. A carrier may be an antiadherent, binder, coating, disintegrant, filler or diluent, preservative (such as antioxidant, antibacterial, or antifungal agent), sweetener, absorption delaying agent, wetting agent, emulsifying agent, buffer, and the like. Examples of suitable pharmaceutically acceptable carriers include water, ethanol, polyols (such as glycerol, propylene glycol, polyethylene glycol, and the like), dextrose, vegetable oils (such as olive oil), saline, buffer, buffered saline, and isotonic agents such as sugars, polyalcohols, sorbitol, and sodium chloride.

The term "subject" (alternatively "patient") as used herein refers to a mammal that has been the object of treatment, observation, or experiment. The mammal may be male or female. The mammal may be one or more selected from the group consisting of humans, bovine (e.g., cows), porcine (e.g., pigs), ovine (e.g., sheep), capra (e.g., goats), equine (e.g., horses), canine (e.g., domestic dogs), feline (e.g., house cats), Lagomorpha (rabbits), rodents (e.g., rats or mice), *Procyon lotor* (e.g., raccoons). In particular embodiments, the subject is human. The term "subject in need thereof" as used herein refers to a subject diagnosed with, or suspected of having, a cell-proliferation disorder, such as a cancer, as defined herein.

As used herein, the terms "treatment" and "treating" refer to all processes in which there may be a slowing, interrupting, arresting, controlling, or stopping of the progression of a disease or disorder described herein. The terms do not necessarily indicate a total elimination of all disease or disorder symptoms.

"Variable regions" or "V region" or "V chain" as used herein means the segment of IgG chains which is variable in sequence between different antibodies. A "variable region" of an antibody refers to the variable region of the antibody light chain or the variable region of the antibody heavy chain, either alone or in combination. Typically, the variable regions of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3, and FR4. The assignment of amino acids to each domain is, generally, in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342: 878-883.

"Chimeric antibody" refers to an antibody in which a portion of the heavy and/or light chain contains sequences derived from a particular species (e.g., human) or belonging to a particular antibody class or subclass, while the remainder of the chain(s) is derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences or derivatives thereof. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences or derivatives thereof, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" may be added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

"Biotherapeutic agent" means a biological molecule, such as an antibody or fusion protein, that blocks ligand/receptor signaling in any biological pathway that supports tumor maintenance and/or growth or suppresses the anti-tumor immune response.

"Chemotherapeutic agent" refers to a chemical or biological substance that can cause death of cancer cells, or interfere with growth, division, repair, and/or function of cancer cells. Examples of chemotherapeutic agents include those that are disclosed in WO2006/129163, and US20060153808. Classes of chemotherapeutic agents include, but are not limited to: alkylating agents, antimetabolites, kinase inhibitors, spindle poison, plant alkaloids, cytoxic/antitumor antibiotics, topisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, and anti-sense oligonucleotides that inhibit expression of genes implicated in abnormal cell-proliferation or tumor growth. Chemotherapeutic agents useful in the treatment methods of the present disclosure include cytostatic and/or cytotoxic agents.

The therapeutic agents and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The therapeutic agents and compositions of the disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific therapeutic agent being used, the rate of absorption desired, specific formulation or dosage form used, type or severity of the disorder being treated, the specific site of action, and conditions of the patient, and can be readily selected by a person skilled in the art.

The term "simultaneous administration" as used herein in relation to the administration of medicaments refers to the administration of medicaments such that the individual medicaments are present within a subject at the same time. In addition to the concomitant administration of medicaments (via the same or alternative routes), simultaneous administration may include the administration of the medicaments (via the same or an alternative route) at different times.

"Chothia" as used herein means an antibody numbering system described in Al-Lazikani et al., *JMB* 273:927-948 (1997).

"Conservatively modified variants" or "conservative substitution" refers to substitutions of amino acids in a protein with other amino acids having similar characteristics (e.g., charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987)

Molecular Biology of the Gene, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition.

"Diagnostic anti-PD-L monoclonal antibody" means a mAb that specifically binds to the mature form of the designated PD-L (PD-L1 or PDL2) expressed on the surface of certain mammalian cells. A mature PD-L lacks the presecretory leader sequence, also referred to as leader peptide. The terms "PD-L" and "mature PD-L" are used interchangeably herein, and shall be understood to mean the same molecule unless otherwise indicated or readily apparent from the context.

As used herein, a diagnostic anti-human PD-L1 mAb or an anti-hPD-L1 mAb refers to a monoclonal antibody that specifically binds to mature human PD-L1. A mature human PD-L1 molecule consists of amino acids 19-290 set forth in SEQ ID NO 21 (Table 3).

Specific examples of diagnostic anti-human PD-L1 mAbs useful as diagnostic mAbs for IHC detection of PD-L1 expression in FFPE tumor tissue sections are antibodies 20C3 and 22C3, which are described in PCT International Patent Application Publication No. WO2014/100079. Another anti-human PD-L1 mAb that has been reported to be useful for IHC detection of PD-L1 expression in FFPE tissue sections (Chen, B. J. et al., *Clin Cancer Res* 19: 3462-3473 (2013)) is a rabbit anti-human PD-L1 mAb publicly available from Sino Biological, Inc. (Beijing, P.R. China; Catalog number 10084-R015).

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared×100. For example, if 8 of 10 of the positions in two sequences are matched when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

The term "isolated" as used in reference to an antibody or fragment thereof refers to the purification status and, in such context, means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

"RECIST 1.1 Response Criteria" as used herein means the definitions set forth in Eisenhauer, E. A. et al., *Eur. J. Cancer* 45:228-247 (2009) for target lesions or nontarget lesions, as appropriate based on the context in which response is being measured.

"Sustained response" means a sustained therapeutic effect after cessation of treatment as described herein. In some embodiments, the sustained response has a duration that is at least the same as the treatment duration, or at least 1.5, 2.0, 2.5 or 3 times longer than the treatment duration.

"Tissue Section" refers to a single part or piece of a tissue, e.g., a thin slice of tissue cut from a sample of a normal tissue or of a tumor.

"Treat" or "treating" a cell-proliferation disorder as used herein means to administer a combination therapy of an anti-human PD-1 antibody (or antigen binding fragment thereof) and a CXCR2 antagonist to a subject having a cell-proliferation disorder, such as cancer, or diagnosed with a cell-proliferation disorder, such as cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Such "treatment" may result in a slowing, interrupting, arresting, controlling, or stopping of the progression of a cell-proliferation disorder as described herein but does not necessarily indicate a total elimination of the cell-proliferation disorder or the symptoms of the cell-proliferation disorder. Positive therapeutic effects in cancer can be measured in a number of ways (See, W. A. Weber, *J. Nucl. Med.* 50:1S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some embodiments, the treatment achieved by a combination therapy of the disclosure is any of PR, CR, OR, PFS, DFS, and OS. PFS, also referred to as "Time to Tumor Progression" indicates the length of time during and after treatment that the cancer does not grow, and includes the amount of time patients have experienced a CR or PR, as well as the amount of time patients have experienced SD. DFS refers to the length of time during and after treatment that the patient remains free of disease. OS refers to a prolongation in life expectancy as compared to naive or untreated individuals or patients. In some embodiments, response to a combination therapy of the disclosure is any of PR, CR, PFS, DFS, or OR that is assessed using RECIST 1.1 response criteria. The treatment regimen for a combination therapy of the disclosure that is effective to treat a cancer patient may vary according to factors such as the disease state, age, and weight of the patient, and the ability of the therapy to elicit an anti-cancer response in the subject. While an embodiment of any of the aspects of the disclosure may not be effective in achieving a positive therapeutic effect in every subject, it should do so in a statistically significant number of subjects as determined by any statistical test known in the art such as the Student's t-test, the $\text{chi}^2$-test, the U-test according to Mann and Whitney, the Kruskal-Wallis test (H-test), Jonckheere-Terpstra-test and the Wilcoxon-test.

As used herein, the terms "combination therapy" and "therapeutic combination" refer to treatments in which at least one anti-human PD-1 antibody (or antigen-binding fragment thereof) and at least one CXCR2 antagonist, and optionally additional therapeutic agents, each are administered to a patient in a coordinated manner, over an overlapping period of time. The period of treatment with the at least one anti-human PD-1 antibody (or antigen-binding fragment thereof) (the "anti-PD-1 treatment") is the period of time that a patient undergoes treatment with the anti-human PD-1 antibody (or antigen-binding fragment thereof); that is, the period of time from the initial dosing with the anti-human PD-1 antibody (or antigen-binding fragment thereof) through the final day of a treatment cycle. Similarly, the period of treatment with the at least one CXCR2 antagonist (the "CXCR2 antagonist treatment") is the period of time that a patient undergoes treatment with the CXCR2 antagonist; that is, the period of time from the initial dosing with the CXCR2 antagonist through the final day of a treatment cycle. In the methods and therapeutic combinations described herein, the anti-PD-1 treatment overlaps by at least one day the CXCR2 antagonist treatment. In certain embodiments, the anti-PD-1 treatment and the CXCR2 antagonist treatment are coextensive. In embodiments, the anti-PD-1 treatment begins prior to the CXCR2 antagonist treatment. In embodiments, the CXCR2 antagonist treatment begins prior to the anti-PD-1 treatment. In embodiments, the anti-PD-1 treatment is terminated prior to termination of CXCR2 antagonist treatment. In embodiments, the CXCR2 antagonist treatment is terminated prior to termination of the anti-PD-1 treatment.

The terms "treatment regimen", "dosing protocol", and "dosing regimen" are used interchangeably to refer to the dose and timing of administration of each therapeutic agent in a combination therapy of the disclosure.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Advanced solid tumor malignancy" and "advanced solid tumor" are used interchangeably to refer to a tumor for which curative resection is not possible. Advanced solid tumors include, but are not limited to, metastatic tumors in bone, brain, breast, liver, lungs, lymph node, pancreas, prostate, and soft tissue (sarcoma).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g., by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using calipers, or while in the body using imaging techniques, e.g., bone scan, ultrasound, CT or MRI scans.

It is understood that wherever embodiments are described herein with the language "comprising," otherwise analogous embodiments described in terms of "consisting of" and/or "consisting essentially of" are also provided.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between. Numerical values provided herein, and the use of the term "about", may include variations of ±1%, ±2%, ±3%, ±4%, ±5%, ±10%, ±15%, and ±20% and their numerical equivalents. All ranges also are intended to include all included sub-ranges, although not necessarily explicitly set forth. For example, a range of 3 to 7 days is intended to include 3, 4, 5, 6, and 7 days. In addition, the term "or," as used herein, denotes alternatives that may, where appropriate, be combined; that is, the term "or" includes each listed alternative separately as well as their combination.

Where aspects or embodiments of the disclosure are described in terms of a Markush group or other grouping of alternatives, the present disclosure encompasses not only the entire group listed as a whole, but each member of the group individually and all possible subgroups of the main group, but also the main group absent one or more of the group members. The present disclosure also envisages the explicit exclusion of one or more of any of the group members in the claims.

Unless otherwise defined, all technical and scientific terms used herein have the same meaning as commonly understood by one of ordinary skill in the art to which this disclosure relates. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Exemplary methods and materials are described herein, although methods and materials similar or equivalent to those described herein can also be used in the practice or testing of the present disclosure. The materials, methods, and examples are illustrative only and not intended to be limiting.

The present disclosure relates to methods of treating a cell-proliferation disorder as defined herein, wherein the method comprises administering to a human patient in need thereof a combination therapy that comprises (a) an anti-human PD-1 antibody (or antigen-binding fragment thereof); and (b) a CXCR2 antagonist.

The present disclosure also relates to a therapeutic combination, wherein the therapeutic combination comprises (a) an anti-human PD-1 antibody (or antigen-binding fragment thereof); and (b) a CXCR2 antagonist.

In some embodiments of the methods and the therapeutic combination, the anti-human PD-1 antibody is pembrolizumab and the CXCR2 antagonist is the compound of Formula I. In some embodiments of the methods and the therapeutic combination, the CXCR2 antagonist is navarixin.

Anti-PD-1 Antibodies and Antigen-Binding Fragments Thereof

The invention provides therapeutic combinations comprising antibodies or antigen binding fragments thereof, which specifically bind to human PD-1 (e.g., a human or humanized anti-PD-1 antibody) and a CXCR2 antagonist, as well as methods for using the therapeutic combinations of the invention. Any anti-human PD-1 antibody or antigen binding fragment thereof can be used in the therapeutic combinations and methods of the invention. In particular embodiments, the anti-human PD-1 antibody is selected from pembrolizumab and nivolumab. In specific embodiments, the anti-human PD-1 antibody is pembrolizumab. In alternative embodiments, the anti-human PD-1 antibody is nivolumab. Table 2 provides amino acid sequences for exemplary anti-human PD-1 antibodies pembrolizumab and nivolumab In some embodiments, an anti-human PD-1 antibody or antigen binding fragment thereof for use in the therapeutic combinations and methods of the invention comprises three light chain CDRs of CDRL1, CDRL2 and CDRL3 and/or three heavy chain CDRs of CDRH1, CDRH2 and CDRH3.

In one embodiment of the invention, CDRL1 is SEQ ID NO:1 or a variant of SEQ ID NO:1, CDRL2 is SEQ ID NO:2 or a variant of SEQ ID NO:2, and CDRL3 is SEQ ID NO:3 or a variant of SEQ ID NO:3.

In one embodiment, CDRH1 is SEQ ID NO:6 or a variant of SEQ ID NO:6, CDRH2 is SEQ ID NO: 7 or a variant of SEQ ID NO:7, and CDRH3 is SEQ ID NO:8 or a variant of SEQ ID NO:8.

In one embodiment, the three light chain CDRs are SEQ ID NO:1, SEQ ID NO:2, and SEQ ID NO:3 and the three heavy chain CDRs are SEQ ID NO:6, SEQ ID NO:7 and SEQ ID NO:8.

In an alternative embodiment of the invention, CDRL1 is SEQ ID NO:11 or a variant of SEQ ID NO:11, CDRL2 is SEQ ID NO:12 or a variant of SEQ ID NO:12, and CDRL3 is SEQ ID NO:13 or a variant of SEQ ID NO:13.

In one embodiment, CDRH1 is SEQ ID NO:16 or a variant of SEQ ID NO:16, CDRH2 is SEQ ID NO:17 or a variant of SEQ ID NO:17, and CDRH3 is SEQ ID NO:18 or a variant of SEQ ID NO:18.

In one embodiment, the three light chain CDRs are SEQ ID NO:1, SEQ ID NO:2, and SEQ ID NO:3 and the three heavy chain CDRs are SEQ ID NO:6, SEQ ID NO:7 and SEQ ID NO:8.

In an alternative embodiment, the three light chain CDRs are SEQ ID NO:11, SEQ ID NO:12, and SEQ ID NO:13 and the three heavy chain CDRs are SEQ ID NO:16, SEQ ID NO:17 and SEQ ID NO:18.

Some antibody and antigen binding fragments used in the therapeutic combinations and methods of the invention comprise a light chain variable region and a heavy chain variable region. In some embodiments, the light chain variable region comprises SEQ ID NO:4 or a variant of SEQ ID NO:4, and the heavy chain variable region comprises SEQ ID NO:9 or a variant of SEQ ID NO:9. In further embodiments, the light chain variable region comprises SEQ ID NO:14 or a variant of SEQ ID NO:14, and the heavy chain variable region comprises SEQ ID NO:19 or a variant of SEQ ID NO:19. In such embodiments, a variant light chain or heavy chain variable region sequence is identical to the reference sequence except having one, two, three, four or five amino acid substitutions. In some embodiments, the substitutions are in the framework region (i.e., outside of the CDRs). In some embodiments, one, two, three, four or five of the amino acid substitutions are conservative substitutions.

In one embodiment of the therapeutic combinations and methods of the invention, the antibody or antigen binding fragment comprises a light chain variable region comprising or consisting of SEQ ID NO:4 and a heavy chain variable region comprising or consisting SEQ ID NO:9. In a further embodiment, the antibody or antigen binding fragment comprises a light chain variable region comprising or consisting of SEQ ID NO:14 and a heavy chain variable region comprising or consisting of SEQ ID NO:19.

In another embodiment, the therapeutic combinations and methods of the invention comprise an antibody or antigen binding protein that has a $V_L$ domain and/or a $V_H$ domain with at least 95%, 90%, 85%, 80%, 75% or 50% sequence homology to one of the $V_L$ domains or $V_H$ domains described above, and exhibits specific binding to PD-1. In another embodiment, the antibody or antigen binding protein of the therapeutic combinations and methods of the invention comprises $V_L$ and $V_H$ domains having up to 1, 2, 3, 4, or 5 or more amino acid substitutions, and exhibits specific binding to PD-1.

In any of the embodiments above, the therapeutic combinations and methods may use a full-length anti-PD-1 antibody or an antigen binding fragment thereof that specifically binds human PD-1. In certain embodiments, a full-length anti-human PD-1 antibody selected from any class of immunoglobulins, including IgM, IgG, IgD, IgA, and IgE is used. Preferably, the antibody is an IgG antibody. Any isotype of IgG can be used, including $IgG_1$, $IgG_2$, $IgG_3$, and $IgG_4$. Different constant domains may be appended to the $V_L$ and $V_H$ regions provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

In embodiments of the invention, the therapeutic combinations and methods use an anti-human PD-1 antibody comprising a light chain comprising or consisting of a sequence of amino acid residues as set forth in SEQ ID NO:5 and a heavy chain comprising or consisting of a sequence of amino acid residues as set forth in SEQ ID NO:10. In alternative embodiments, the therapeutic combinations and methods use an anti-human PD-1 antibody comprising a light chain comprising or consisting of a sequence of amino acid residues as set forth in SEQ ID NO:15 and a heavy chain comprising or consisting of a sequence of amino acid residues as set forth in SEQ ID NO:20. In some therapeutic combinations and methods of the invention, the anti-human PD-1 antibody is pembrolizumab or a pembrolizumab biosimilar. In some therapeutic combinations and methods of the invention, the anti-human PD-1 antibody is nivolumab or a nivolumab biosimilar.

Ordinarily, amino acid sequence variants of the anti-PD-1 antibodies and antigen binding fragments used in the invention will have an amino acid sequence having at least 75% amino acid sequence identity with the amino acid sequence of a reference antibody or antigen binding fragment (e.g., heavy chain, light chain, $V_H$, $V_L$, or humanized sequence), more preferably at least 80%, more preferably at least 85%, more preferably at least 90%, and most preferably at least 95, 98, or 99%. Identity or homology with respect to a sequence is defined herein as the percentage of amino acid residues in the candidate sequence that are identical with the anti-PD-1 residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

Sequence identity refers to the degree to which the amino acids of two polypeptides are the same at equivalent positions when the two sequences are optimally aligned. Sequence identity can be determined using a BLAST algorithm wherein the parameters of the algorithm are selected to give the largest match between the respective sequences over the entire length of the respective reference sequences. The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

TABLE 2

Exemplary PD-1 Antibody Sequences

| Antibody Feature | Amino Acid Sequence | SEQ ID NO. |
|---|---|---|
| *Pembrolizumab Light Chain* | | |
| CDR1 | RASKGVSTSGYSYLH | 1 |
| CDR2 | LASYLES | 2 |
| CDR3 | QHSRDLPLT | 3 |
| Variable Region | EIVLTQSPATLSLSPGERATLSCRASKGVSTSGYSYLHWYQQKPGQAPRLLIYLASYLESGVPARFSGSGSGTDFTLTISSLEPEDFAVYYCQHSRDLPLTFGGGTKVEIK | 4 |
| Light Chain | EIVLTQSPATLSLSPGERATLSCRASKGVSTSGYSYLHWYQQKPGQAPRLLIYLASYLESGVPARFSGSGSGTDFTLTISSLEPEDFAVYYCQHSRDLPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 5 |
| *Pembrolizumab Heavy Chain* | | |
| CDR1 | NYYMY | 6 |
| CDR2 | GINPSNGGTNFNEKFKN | 7 |
| CDR3 | RDYRFDMGFDY | 8 |
| Variable Region | QVQLVQSGVEVKKPGASVKVSCKASGYTFTNYYMYWVRQAPGQGLEWMGGINPSNGGTNFNEKFKNRVTLTTDSSTTTAYMELKSLQFDDTAVYYCARRDYRFDMGFDYWGQGTTVTVSS | 9 |
| Heavy Chain | QVQLVQSGVEVKKPGASVKVSCKASGYTFTNYYMYWVRQAPGQGLEWMGGINPSNGGTNFNEKFKNRVTLTTDSSTTTAYMELKSLQFDDTAVYYCARRDYRFDMGFDYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 10 |
| *Nivolumab Light Chain* | | |
| CDR1 | RASQSVSSYLA | 11 |
| CDR2 | DASNRAT | 12 |
| CDR3 | QQSSNWPRT | 13 |
| Variable Region | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK | 14 |
| Light Chain | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLS SPVTKSFNRGEC | 15 |
| *Nivolumab Heavy Chain* | | |
| CDR1 | NSGMH | 16 |
| CDR2 | VIWYDGSKRYYADSVKG | 17 |
| CDR3 | NDDY | 18 |

TABLE 2-continued

Exemplary PD-1 Antibody Sequences

| Antibody Feature | Amino Acid Sequence | SEQ ID NO. |
|---|---|---|
| Variable Region | QVQLVESGGGVVQPGRSLRLDCKASGITFSNSGMHWVR QAPGKGLEWVAVIWYDGSKRYYADSVKGRFTISRDNSK NTLFLQMNSLRAEDTAVYYCATNDDYWGQGTLVTVSS | 19 |
| Heavy Chain | QVQLVESGGGVVQPGRSLRLDCKASGITFSNSGMHWVR QAPGKGLEWVAVIWYDGSKRYYADSVKGRFTISRDNSK NTLFLQMNSLRAEDTAVYYCATNDDYWGQGTLVTVSSA STKGPSVFPLAPCSRSTSESTAALGCLVKDYFPEPVTVSW NSGALTSGVHTFPAVLQSSGLYSLSSVVTVPSSSLGTKTY TCNVDHKPSNTKVDKRVESKYGPPCPPCPAPEFLGGPSVF LFPPKPKDTLMISRTPEVTCVVVDVSQEDPEVQFNWYVD GVEVHNAKTKPREEQFNSTYRVVSVLTVLHQDWLNGKE YKCKVSNKGLPSSIEKTISKAKGQPREPQVYTLPPSQEEM TKNQVSLTCLVKGFYPSDIAVEWESNGQPENNYKTTPPV LDSDGSFFLYSRLTVDKSRWQEGNVFSCSVMHEALHNH YTQKSLSLSLGK | 20 |

TABLE 3

Human PD-L1 Sequence (amino acid residues 19-290)

| Protein | Amino Acid Sequence | SEQ ID NO. |
|---|---|---|
| Human PD-L1 (aa 19-290) | MRIFAVFIFMTYWHLLNAFTVTVPKDLYVVEY GSNMTIECKFPVEKQLDLAALIVYWEMEDKNI IQFVHGEEDLKVQHSSYRQRARLLKDQLSLGN AALQITDVKLQDAGVYRCMISYGGADYKRITV KVNAPYNKINQRILVVDPVTSEHELTCQAEGY PKAEVIWTSSDHQVLSGKTTTTNSKREEKLFN VTSTLRINTTTNEIFYCTFRRLDPEENHTAEL VIPELPLAHPPNERTHLVILGAILLCLGVALT FIFRLRKGRMMDVKKCGIQDTNSKKQSDTHLE ET | 21 |

"PD-L1" expression expression as used herein means any detectable level of expression of the designated PD-L protein on the cell surface or of the designated PD-L mRNA within a cell or tissue. PD-L protein expression may be detected with a diagnostic PD-L antibody in an IHC assay of a tumor tissue section or by flow cytometry. Alternatively, PD-L protein expression by tumor cells may be detected by PET imaging, using a binding agent (e.g., antibody fragment, affibody, and the like) that specifically binds to PD-L1. Techniques for detecting and measuring PD-L mRNA expression include RT-PCR and realtime quantitative RT-PCR.

Several approaches have been described for quantifying PD-L1 protein expression in IHC assays of tumor tissue sections. See, e.g., Thompson, R. H., et al., *PNAS* 101 (49); 17174-17179 (2004); Thompson, R. H. et al., *Cancer Res.* 66:3381-3385 (2006); Gadiot, J., et al., *Cancer* 117:2192-2201 (2011); Taube, J. M. et al., *Sci Transl Med* 4, 127ra37 (2012); and Toplian, S. L. et al., *New Eng. J Med.* 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression is at least 1%, and preferably 5% of total tumor cells.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is ≥5.

The level of PD-L1 mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue. In some embodiments, PD-L1 expression in a tumor sample is determined to be elevated if PD-L1 protein (and/or PD-L1 mRNA) in the sample is at least 10%, 20%, 30%, or 50% greater than in the control.

CXCR2 Antagonists

CXCR2 antagonists useful in the methods and therapeutic compositions of the invention are compounds of the Formula I

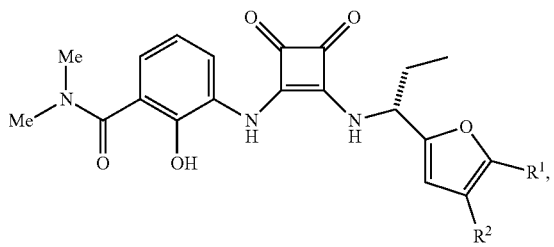

wherein $R^1$ are $R^2$ are independently H or $C_1$-$C_5$ alkyl or a pharmaceutically acceptable salt thereof. Compounds of the Formula I, pharmaceutically acceptable salts and are described in International Publ. No. WO 02/083624, published Oct. 24, 2002.

One preferred CXCR2 antagonist for use in the methods and therapeutic combinations of the invention is 2-hydroxy-N,N-dimethyl-3-{2-[[(R)-1-(5-methylfuran-2-yl)propyl]amino]-3,4-dioxocyclobut-1-enylamino}benzamide, (also known as navarixin) which has the structural formula below:

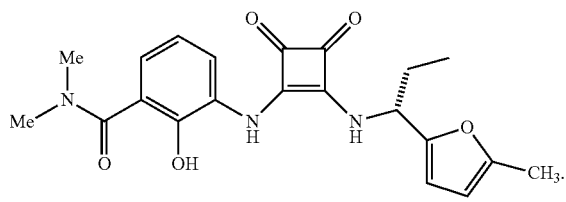 [SMILES: CC[C@@H](Nc1c(Nc2cccc(C(=O)N(C)C)c2O)c(=O)c1=O)c1ccc(C)o1]

Navarixin and its pharmacology are described in Dwyer, M. P. et al., *J. Med. Chem.*, 2006, 49 (26), pp 7603-7606. The preparation of navarixin is described in U.S. Patent Appl. Publ. No. 2004/0209946 in Examples 1 and 2, and in U.S. Patent Appl. Publ. No. US2011/0160469 in Example IIB.

Another preferred CXCR2 antagonist for use in the methods and therapeutic combinations of the invention is the compound having the structural formula below:

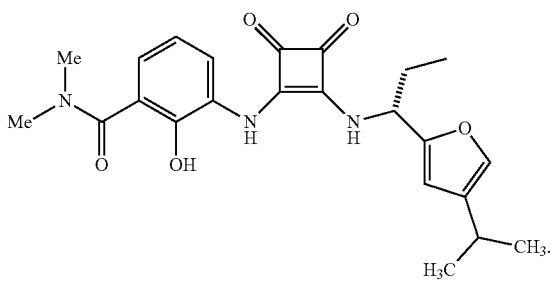 [SMILES: CC[C@@H](Nc1c(Nc2cccc(C(=O)N(C)C)c2O)c(=O)c1=O)c1cc(C(C)C)co1]

The preparation of this compound is disclosed in U.S. Pat. No. 7,132,445 in Example 360.106.

Salts

As indicated above, the compounds of the present invention can be employed in the form of pharmaceutically acceptable salts. Those skilled in the art will recognize those instances in which the compounds of the invention may form salts. Examples of such compounds are described herein by reference to possible salts. Such reference is for illustration only. Pharmaceutically acceptable salts can be used with compounds for treating patients. Non-pharmaceutical salts may, however, be useful in the preparation of intermediate compounds.

The term "pharmaceutically acceptable salt" refers to a salt (including an inner salt such as a zwitterion) that possesses effectiveness similar to the parent compound and that is not biologically or otherwise undesirable (e.g., is neither toxic nor otherwise deleterious to the recipient thereof). Thus, an embodiment of the invention provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Additionally, acids that are generally considered suitable for the formation of pharmaceutically useful salts from basic pharmaceutical compounds are discussed, for example, by P. Stahl et al, Camille G. (eds.), *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

All such acid salts and base salts are intended to be pharmaceutically acceptable salts within the scope of the invention and all acid and base salts are considered equivalent to the free forms of the corresponding compounds for purposes of the invention.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is understood that certain compounds of the invention may exist in zwitterionic form, having both anionic and cationic centers within the same compound and a net neutral charge. Such zwitterions are included within the invention.

Administration

The present disclosure relates to methods of treating a cell-proliferation disorder, said method comprising administering to a subject in need thereof a combination therapy that comprises (a) an anti-human PD-1 antibody (or antigen-binding fragment thereof); and (b) a CXCR2 antagonist.

Anti-PD-1 antibodies, or antigen-binding fragments thereof, may be provided by continuous infusion, or by doses administered, e.g., daily, 1-7 times per week, weekly, bi-weekly, tri-weekly, monthly, bimonthly, quarterly, semi-annually, annually etc. Doses may be provided, e.g., intravenously, subcutaneously, topically, orally, nasally, rectally, intramuscular, intracerebrally, intraspinally, or by inhalation. In certain embodiments, the doses are provided intravenously or subcutaneously. A total dose for a treatment interval is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) New Engl. J. Med. 349:427-434; Herold, et al. (2002) New Engl. J. Med. 346:1692-1698; Liu, et al. (1999) J. Neurol. Neurosurg. Psych. 67:451-456; Portielji, et al. (20003) Cancer Immunol. Immunother. 52:133-144). Doses may also be provided to achieve a pre-determined target concentration of anti-human PD-1 antibody (or antigen-binding fragment thereof) in the subject's serum, such as 0.1, 0.3, 1, 3, 10, 30, 100, 300 µg/mL or more. In embodiments, the anti-human PD-1 antibody (or antigen-binding fragment thereof) is administered as a 200 mg dose once every 21 days. In other embodiments, anti-PD-1 antibodies (or antigen-binding fragments thereof) are administered subcutaneously or intravenously, on a weekly, biweekly, "every 4 weeks," monthly, bimonthly, or quarterly basis at 10, 20, 50, 80, 100, 200, 500, 1000 or 2500 mg/subject.

The CXCR2 antagonists and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. In embodiments, the CXCR2 antagonist may be formulated into a dosage form that allows for systemic use, i.e., distribution of CXCR2 antagonist throughout the body of the subject; examples of such systemic administration include oral administration and intravenous administration. In additional embodiments, the CXCR2 antagonist may be formulated into a dosage form that allows for targeted or isolated use, i.e., administration of the CXCR2 antagonist only to the portion of the subject's body to be treated; examples of such targetted administration include intratumoral injection.

The CXCR2 antagonist is administered once every 1 to 30 days. In embodiments, the CXCR2 antagonist is administered once every 3 to 28 days. In particular embodiments, the CXCR2 antagonist is administered once every 3, 7, 14, 21, or 28 days. In embodiments of such methods, the CXCR2 antagonist is administered for from 2 to 36 months. In specific embodiments, the CXCR2 antagonist is administered for up to 3 months. In additional embodiments of such methods, the CXCR2 antagonist is administered once every 3, 7, 14, 21, or 28 days for from 2 to 36 months. In further embodiments, the CXCR2 antagonist is administered once every 3, 7, 14, 21, or 28 days for up to 3 months. In specific embodiments, the CXCR2 antagonist is administered once every 3, 7, 14, 21, or 28 days for up to 3 months, followed by a period, lasting at least 2 months, in which the time interval between doses is increased by at least two-fold. In more specific embodiments, the CXCR2 antagonist is administered once every 3, 7, 14, 21, or 28 days for up to 3 months, followed by a period, lasting at least 2 months, in which the time interval between doses is increased by at least three-fold. For example, if the CXCR2 antagonist is administered once every 7 days for up to 3 months, it may be followed by a period in which the CXCR2 antagonist is administered once every 14 or 21 days for up to two years.

In some embodiments, at least one of the therapeutic agents (the anti-PD-1 antibody, or binding fragment thereof, and the CXCR2 antagonist) in the combination therapy is administered using the same dosage regimen (dose, frequency, and duration of treatment) that is typically employed when the agent is used as monotherapy for treating the same condition. In other embodiments, the patient receives a lower total amount of at least one of the therapeutic agents in the combination therapy than when the agent is used as monotherapy, e.g., smaller doses, less frequent doses, and/or shorter treatment duration.

A combination therapy of the invention may be used prior to or following surgery to remove a tumor and may be used prior to, during, or after radiation treatment.

In some embodiments, a combination therapy of the invention is administered to a patient who has not previously been treated with a biotherapeutic or chemotherapeutic agent, i.e., is treatment-naïve. In other embodiments, the combination therapy is administered to a patient who failed to achieve a sustained response after prior therapy with the biotherapeutic or chemotherapeutic agent, i.e., is treatment-experienced.

Thus, the present disclosure relates to methods of treating a cell-proliferation disorder, said method comprising administering to a subject in need thereof a combination therapy that comprises (a) an anti-human PD-1 antibody (or antigen-binding fragment thereof); and (b) a CXCR2 antagonist; wherein the anti-human PD-1 antibody (or antigen-binding fragment thereof) is administered once every 21 days; and the CXCR2 antagonist is administered once every 1 to 30 days for 3 to 90 days, then optionally once every 1 to 30 days for up to 1050 days. In embodiments, the CXCR2 antagonist is administered at least three times.

In specific embodiments, the CXCR2 antagonist is administered once every 3 to 30 days for 9 to 90 days, then optionally once every 3 to 30 days for up to 1050 days. In specific embodiments, the CXCR2 antagonist is administered once every 3 to 21 days for 9 to 63 days, then optionally once every 3 to 21 days for up to 735 days. In further specific embodiments, the CXCR2 antagonist is administered once every 7 to 21 days for 21 to 63 days, then optionally once every 7 to 21 days for up to 735 days. In still further embodiments, the CXCR2 antagonist is administered once every 7 to 10 days for 21 to 30 days, then optionally once every 21 days for up to 735 days. In still further embodiments, the CXCR2 antagonist is administered once every 7 days for 21 days, then optionally once every 21 days for up to 735 days. In additional embodiments, the CXCR2 antagonist is administered once every 21 days for 63 days, then optionally once every 21 days for up to 735 days. In specific embodiments of the foregoing, the CXCR2 antagonist is administered at least three times.

In some embodiments, one or more optional "rest" periods, during which the CXCR2 antagonist is not administered, may be included in the treatment period. In specific embodiments, the optional rest period may be for from 3 to 30 days, from 7 to 21 days, or from 7 to 14 days. Following the rest period, dosing of the CXCR2 antagonist may be resumed as described above.

Cell-Proliferation Disorders

The combination therapies disclosed herein are potentially useful in treating diseases or disorders including, but not limited to, cell-proliferation disorders. Cell-proliferation disorders include, but are not limited to, cancers, benign papillomatosis, and gestational trophoblastic diseases. The terms "cancer", "cancerous", or "malignant" refer to or describe the physiological condition in mammals that is typically characterized by unregulated cell growth. A variety of cancers where PD-L1 or PD-L2 are implicated, whether malignant or benign and whether primary or secondary, may be treated or prevented with a method provided by the disclosure. Particularly preferred cancers that may be treated in accordance with the present disclosure include those characterized by elevated expression of one or both of PD-L1 and PD-L2 in tested tissue samples.

The disease or disorder to be treated is a cell-proliferation disorder. In certain embodiments, the cell-proliferation disorder is cancer. In particular embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, metastatic, microsatellite instability-high (MSI-H) cancer, mismatch repair deficient cancer, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary origin (i.e., cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In specific embodiments, the cancer is selected from brain and spinal cancers. In particular embodiments, the brain and spinal cancer is selected from the group consisting of anaplastic astrocytomas, glioblastomas, astrocytomas, and estheosioneuroblastomas (also known as olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, a typical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sP-NET).

In specific embodiments, the cancer is selected from cancers of the head and neck, including recurrent or metastatic head and neck squamous cell carcinoma (HNSCC), nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers. In specific embodiments, the skin cancer is unresectable or metastatic melanoma.

In specific embodiments, the cancer is selected from cancers of the reproductive system. In particular embodiments, the cancer is selected from the group consisting of breast cancers, cervical cancers, vaginal cancers, ovarian cancers, endometrial cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In more specific instances of these embodiments, the breast cancer is triple-negative breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gall bladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gall bladder adenocarcinomas, colorectal adenocarcinomas, and anal squamous cell carcinomas.

In specific embodiments, the cancer is selected from liver and bile duct cancers. In particular embodiments, the cancer is liver cancer (also known as hepatocellular carcinoma). In particular embodiments, the cancer is bile duct cancer (also known as cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urothelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, chordoma (cancer of the bone along the spine).

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., classical Hodgkin refractory lymphoma), non-Hodgkin lymphoma (e.g., diffuse large B-cell lymphoma, follicular lymphoma, mycosis fungoides, Sezary syndrome, primary central nervous system lymphoma), cutaneous T-cell lymphomas, primary central nervous system lymphomas.

In specific embodiments, the cancer is selected from glandular cancers. In particular embodiments, the cancer is selected from the group consisting of adrenocortical cancer (also known as adrenocortical carcinoma or adrenal cortical carcinoma), pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In specific embodiments, the cell-proliferation disorder is selected from benign papillomatosis, benign neoplastic diseases and gestational trophoblastic diseases. In particular embodiments, the gestational trophoblastic disease is selected from the group consisting of hydatidiform moles, and gestational trophoblastic neoplasia (e.g., invasive moles, choriocarcinomas, placental-site trophoblastic tumors, and epithelioid trophoblastic tumors).

In embodiments, the cell-proliferation disorder is a cancer that has metastasized, for example, a liver metastases from colorectal cancer.

In embodiments, the cell-proliferation disorder is selected from the group consisting of solid tumors and lymphomas. In particular embodiments, the cell-proliferation disorder is selected from the group consisting of advanced or metastatic solid tumors and lymphomas. In more particular embodiments, the cell-proliferation disorder is selected from the group consisting of malignant melanoma, head and neck squamous cell carcinoma, breast adenocarcinoma, and lymphomas. In aspects of such embodiments, the lymphomas are selected from the group consisting of diffuse large B-cell lymphoma, follicular lymphoma, mantle cell lymphoma, small lymphocytic lymphoma, mediastinal large B-cell lymphoma, splenic marginal zone B-cell lymphoma, extranodal marginal zone B-cell lymphoma of mucosa-associated lymphoid tissue (malt), nodal marginal zone B-cell lymphoma, lymphoplasmacytic lymphoma, primary effusion lymphoma, Burkitt lymphoma, anaplastic large cell lymphoma (primary cutaneous type), anaplastic large cell lymphoma (systemic type), peripheral T-cell lymphoma, angioimmunoblastic T-cell lymphoma, adult T-cell lymphoma/leukemia, nasal type extranodal NK/T-cell lymphoma, enteropathy-associated T-cell lymphoma, gamma/delta hepatosplenic T-cell lymphoma, subcutaneous panniculitis-like T-cell lymphoma, mycosis fungoides, and Hodgkin lymphoma.

In particular embodiments, the cell-proliferation disorder is classified as stage III cancer or stage IV cancer. In instances of these embodiments, the cancer is not surgically resectable.

Methods, Uses, and Medicaments

Products provided as therapeutic combinations may include a composition comprising an anti-human PD-1 antibody (or antigen-binding fragment thereof) and a CXCR2 antagonist together in the same pharmaceutical composition, or may include a composition comprising anti-human PD-1 antibody (or antigen-binding fragment thereof), and a composition comprising a CXCR2 antagonist in separate form, e.g., in the form of a kit or in any form designed to enable separate administration either concurrently or on separate dosing schedules.

The combination therapy may also comprise one or more additional therapeutic agents. The additional therapeutic agent may be, e.g., a chemotherapeutic, a biotherapeutic agent (including but not limited to antibodies or antigen-binding fragments thereof that specifically bind to an antigen selected from the group consisting of: PD-L1, PD-L2, CTLA4, LAG3, BTLA, TIM3, HVEM, GITR, CD27, TIGIT, ILT2, ILT3, ILT4, ILT5, SIRPα, NKG2A, NKG2C, NKG2E, TSLP, IL10, VISTA, VEGF, EGFR, Her2/neu, VEGF receptors, other growth factor receptors, CD20, CD28, CD40, CD-40L, CD70, OX-40, 4-1BB, and ICOS). The one or more additional active agents may be co-administered either with the anti-human PD-1 antibody (or antigen-binding fragment thereof) or with the CXCR2 antagonist. The additional active agent(s) may be administered in a single dosage form with one or more co-administered agent selected from the anti-human PD-1 antibody (or antigen-binding fragment thereof) and the CXCR2 antagonist, or the additional active agent(s) may be administered in separate dosage form(s) from the dosage forms containing the anti-human PD-1 antibody (or antigen-binding fragment thereof) and/or the CXCR2 antagonist.

The therapeutic combination disclosed herein may be used in combination with one or more other active agents, including but not limited to, other anti-cancer agents that are used in the prevention, treatment, control, amelioration, or reduction of risk of a particular disease or condition (e.g., cell-proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

The additional active agent(s) may be one or more agents selected from the group consisting of STING agonists, poly ADP ribose polymerase (PARP) inhibitors, mitogen-activated protein kinase (MEK) inhibitors, cyclin-dependent kinase (CDK) inhibitors, indoleamine 2,3-dioxygenase (IDO) inhibitors, tryptophan 2,3-dioxygenase (TDO) selective inhibitors, anti-viral compounds, antigens, adjuvants, anti-cancer agents, CTLA-4, LAG-3 and PD-1 pathway antagonists, lipids, liposomes, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood the descriptions of the above additional active agents may be overlapping. It will also be understood that the treatment combinations are subject to optimization, and it is understood that the best combination to use of the anti-human PD-1 antibody (or antigen-binding fragment thereof) and/or the CXCR2 antagonist, and one or more additional active agents will be determined based on the individual patient needs.

When the therapeutic combination disclosed herein is used contemporaneously with one or more other active agents, the anti-human PD-1 antibody (or antigen-binding fragment thereof) and/or the CXCR2 antagonist may be administered either simultaneously with, or before or after, one or more other active agent(s). Either of the anti-human PD-1 antibody (or antigen-binding fragment thereof) and/or the CXCR2 antagonist may be administered separately, by the same or different route of administration, or together in the same pharmaceutical composition as the other agent(s).

The weight ratio of the anti-human PD-1 antibody (or antigen-binding fragment thereof) to the CXCR2 antagonist may be varied and will depend upon the therapeutically effective dose of each agent. Generally, a therapeutically effective dose of each will be used. Combinations including at least one anti-human PD-1 antibody (or antigen-binding fragment thereof), at least one CXCR2 antagonist, and other active agents will generally include a therapeutically effective dose of each active agent. In such combinations, the anti-human PD-1 antibody (or antigen-binding fragment thereof) and/or the CXCR2 antagonist disclosed herein and other active agents may be administered separately or in conjunction. In addition, the administration of one element may be prior to, concurrent with, or subsequent to the administration of other agent(s).

In one embodiment, this disclosure provides an anti-human PD-1 antibody (or antigen-binding fragment thereof) and/or a CXCR2 antagonist, and at least one other active agent as a combined preparation for simultaneous, separate or sequential use in therapy. In one embodiment, the therapy is the treatment of a cell-proliferation disorder, such as cancer.

In one embodiment, the disclosure provides a kit comprising two or more separate pharmaceutical compositions, one of which contains a anti-human PD-1 antibody (or antigen-binding fragment thereof) and another of which contains a CXCR2 antagonist. In one embodiment, the kit comprises means for separately retaining said compositions, such as a container, divided bottle, or divided foil packet. A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

The disclosure also provides the use of a CXCR2 antagonist for treating a cell-proliferation disorder, where the patient has previously (e.g., within 24 hours) been treated with an anti-human PD-1 antibody (or antigen-binding fragment thereof). The disclosure also provides the use of an anti-human PD-1 antibody (or antigen-binding fragment thereof) for treating a cell-proliferation disorder, where the patient has previously (e.g., within 24 hours) been treated with a CXCR2 antagonist.

Anti-viral compounds that may be used in combination with the therapeutic combinations disclosed herein include hepatitis B virus (HBV) inhibitors, hepatitis C virus (HCV) protease inhibitors, HCV polymerase inhibitors, HCV NS4A inhibitors, HCV NS5A inhibitors, HCV NS5b inhibitors, and human immunodeficiency virus (HIV) inhibitors.

Antigens and adjuvants that may be used in combination with the therapeutic combinations disclosed herein include B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, lipopolysaccharide (LPS), monophosphoryllipid A, lipoteichoic acid, imiquimod, resiquimod, and in addition retinoic acid-inducible gene I (RIG-I) agonists such as poly I:C, used separately or in combination are also potential adjuvants.

Examples of cytotoxic agents that may be used in combination with the therapeutic combinations disclosed herein include, but are not limited to, arsenic trioxide (sold under the tradename TRISENOX®), asparaginase (also known as L-asparaginase, and *Erwinia* L-asparaginase, sold under the tradenames ELSPAR® and KIDROLASE®).

Chemotherapeutic agents that may be used in combination with the therapeutic combinations disclosed herein include abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-prolyl-1-Lproline-t-butylamide, cachectin, cemadotin, chlorambucil, cyclophosphamide, 3',4'-didehydro-4'deoxy-8'-norvin-caleukoblastine, dinaciclib, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyurea andtaxanes, ifosfamide, liarozole, lonidamine, lomustine, MDV3100, mechlorethamine (nitrogen mustard), melphalan, mivobulin isethionate, rhizoxin, sertenef, streptozocin, mitomycin, methotrexate, taxanes, nilutamide, olaparib, onapristone, paclitaxel, prednimustine, procarbazine, RPR109881, selumetinib, stramustine phosphate, tamoxifen, tasonermin, taxol, tretinoin, vinblastine, vincristine, vindesine sulfate, and vinflunine, and pharmaceutically acceptable salts thereof.

Examples of vascular endothelial growth factor (VEGF) receptor inhibitors include, but are not limited to, bevacizumab (sold under the trademark AVASTIN by Genentech/Roche), axitinib (described in PCT International Patent Publication No. WO01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide. and described in PCT International Patent Application Publication No. WO02/068470), pasireotide (also known as SO 230, and described in PCT International Patent Publication No. WO02/010192), and sorafenib.

Examples of topoisomerase II inhibitors, include but are not limited to, etoposide, and teniposide.

Examples of alkylating agents, include but are not limited to, 5-azacytidine, decitabine, temozolomide, dactinomycin (also known as actinomycin-D, melphalan, altretamine, carmustine, bendamustine, busulfan, carboplatin, lomustine, cisplatin, chlorambucil, cyclophosphamide, dacarbazine, altretamine, ifosfamide, procarbazine, mechlorethamine, streptozocin, thiotepa, and pharmaceutically acceptable salts thereof.

Examples of anti-tumor antibiotics include, but are not limited to, doxorubicin, bleomycin, daunorubicin daunorubicin liposomal (daunorubicin citrate liposome), mitoxantrone, epirubicin, idarubicin, and mitomycin C.

Examples of anti-metabolites include, but are not limited to, claribine, 5-fluorouracil, 6-thioguanine, pemetrexed (sold under the tradename ALIMTA®), cytarabine (also known as arabinosylcytosine (Ara-C)), cytarabine liposomal (also known as Liposomal Ara-C, sold under the tradename DEPOCYT™), decitabine (sold under the tradename DACOGEN®), hydroxyurea and fludarabine, floxuridine, cladribine (also known as 2-chlorodeoxyadenosine (2-CdA), methotrexate (also known as amethopterin, methotrexate sodium (MTX)), and pentostatin.

Examples of retinoids include, but are not limited to, alitretinoin, tretinoin, isotretinoin, and bexarotene.

Additional Embodiments

The present disclosure further relates to methods of treating a cell-proliferation disorder, said method comprising administering to a subject in need thereof a combination therapy that comprises (a) an anti-human PD-1 antibody (or antigen-binding fragment thereof); and (b) a CXCR2 antagonist; wherein the anti-human PD-1 antibody (or antigen-binding fragment thereof) is administered once every 21 days; and the CXCR2 antagonist is administered once every 1 to 30 days. In embodiments, the CXCR2 antagonist is administered once every 3 to 28 days. In particular embodiments, the CXCR2 antagonist is administered once every 3, 7, 14, 21, or 28 days.

In embodiments of such methods, the CXCR2 antagonist is administered for from 2 to 36 months. In specific embodiments, the CXCR2 antagonist is administered for up to 3 months.

In additional embodiments of such methods, the CXCR2 antagonist is administered once every 3, 7, 14, 21, or 28 days for from 2 to 36 months. In further embodiments, the CXCR2 antagonist is administered once every 3, 7, 14, 21, or 28 days for up to 3 months. In specific embodiments, the CXCR2 antagonist is administered once every 3, 7, 14, 21, or 28 days for up to 3 months, followed by a period, lasting at least 2 months, in which the time interval between doses is increased by at least two-fold. In more specific embodiments, the CXCR2 antagonist is administered once every 3, 7, 14, 21, or 28 days for up to 3 months, followed by a period, lasting at least 2 months, in which the time interval between doses is increased by at least three-fold. For example, if the CXCR2 antagonist is administered once every 7 days for up to 3 months, it may be followed by a period in which the CXCR2 antagonist is administered once every 14 or 21 days for up to two years.

The present disclosure further relates to methods of treating a cell-proliferation disorder, said method comprising administering to a subject in need thereof a combination therapy that comprises (a) an anti-human PD-1 antibody (or antigen-binding fragment thereof); and (b) a CXCR2 antagonist; wherein the anti-human PD-1 antibody (or antigen-binding fragment thereof) is administered once every 21 days; and the CXCR2 antagonist is administered once every 1 to 30 days for 3 to 90 days, then optionally once every 1 to 30 days for up to 1050 days. In embodiments, the CXCR2 antagonist is administered at least three times.

In specific embodiments, the CXCR2 antagonist is administered once every 3 to 30 days for 9 to 90 days, then optionally once every 3 to 30 days for up to 1050 days. In specific embodiments, the CXCR2 antagonist is administered once every 3 to 21 days for 9 to 63 days, then optionally once every 3 to 21 days for up to 735 days. In further specific embodiments, the CXCR2 antagonist is administered once every 7 to 21 days for 21 to 63 days, then optionally once every 7 to 21 days for up to 735 days. In still further embodiments, the CXCR2 antagonist is administered once every 7 to 10 days for 21 to 30 days, then optionally once every 21 days for up to 735 days. In still further embodiments, the CXCR2 antagonist is administered once every 7 days for 21 days, then optionally once every 21 days for up to 735 days. In additional embodiments, the CXCR2 antagonist is administered once every 21 days for 63 days, then optionally once every 21 days for up to 735 days. In specific embodiments of the foregoing, the CXCR2 antagonist is administered at least three times.

Additionally, the present disclosure relates to methods of treating a cell-proliferation disorder, said method comprising administering to a subject in need thereof a combination therapy that comprises (a) an anti-human PD-1 antibody (or antigen-binding fragment thereof); and (b) a CXCR2 antagonist; wherein the cell-proliferation disorder is cancer. In specific embodiments, the cancer occurs as one or more solid tumors or lymphomas. In further specific embodiments, the cancer is selected from the group consisting of advanced or metastatic solid tumors and lymphomas. In still further specific embodiments, the cancer is selected from the group consisting of malignant melanoma, head and neck squamous cell carcinoma, MSI-H cancer, MMR deficient cancer, non-small cell lung cancer, urothelial carcinoma, gastric or garoesophageal junction adenocarcinoma, breast adenocarcinoma, and lymphomas. In additional embodiments, the lymphoma is selected from the group consisting of diffuse large B-cell lymphoma, follicular lymphoma, mantle cell lymphoma, small lymphocytic lymphoma, mediastinal large B-cell lymphoma, splenic marginal zone B-cell lymphoma, extranodal marginal zone B-cell lymphoma of mucosa-associated lymphoid tissue (malt), nodal marginal zone B-cell lymphoma, lymphoplasmacytic lymphoma, primary effusion lymphoma, Burkitt lymphoma, anaplastic large cell lymphoma (primary cutaneous type), anaplastic large cell lymphoma (systemic type), peripheral T-cell lymphoma, angioimmunoblastic T-cell lymphoma, adult T-cell lymphoma/leukemia, nasal type extranodal NK/T-cell lymphoma, enteropathy-associated T-cell lymphoma, gamma/delta hepatosplenic T-cell lymphoma, subcutaneous panniculitis-like T-cell lymphoma, mycosis fungoides, and Hodgkin lymphoma. In particular embodiments, the cell-proliferation disorder is a cancer that has metastasized, for example, a liver metastases from colorectal cancer. In additional embodiments, the cell-proliferation disorder is a cancer is classified as stage III cancer or stage IV cancer. In instances of these embodiments, the cancer is not surgically resectable.

In embodiments of the methods disclosed herein, the anti-human PD-1 antibody is an anti-PD-1 monoclonal antibody. In particular aspects of these embodiments, the anti-human PD-1 antibody is selected from the group consisting of nivolumab, pembrolizumab, pidilizumab, and AMP-224. In specific aspects of these embodiments, the anti-human PD-1 antibody is selected from nivolumab and pembrolizumab. In a more specific aspect, the anti-human PD-1 antibody is nivolumab. In a further specific aspect, the anti-human PD-1 antibody is pembrolizumab.

In embodiments of the methods disclosed herein, the anti-human PD-1 antibody (or antigen binding fragment thereof) is administered by intravenous infusion or subcutaneous injection, and the CXCR2 antagonist is administered orally, by intravenous infusion, by intertumoral injection, or by subcutaneous injection.

In embodiments of the methods disclosed herein, the anti-human PD-1 antibody (or antigen binding fragment thereof) is administered by intravenous infusion or subcutaneous injection, and the CXCR2 antagonist is administered orally.

In embodiments of the methods disclosed herein, the anti-human PD-1 antibody (or antigen binding fragment thereof) is administered prior to administration of the CXCR2 antagonist. In alternative embodiments of the methods disclosed herein, the CXCR2 antagonist is administered prior to administration of the anti-human PD-1 antibody (or antigen binding fragment thereof).

In embodiments of the methods disclosed herein, the anti-human PD-1 antibody (or antigen binding fragment thereof) is administered at a dose of 200 mg; and the CXCR2 antagonist is administered at a dose of from 10 µg to 3000 µg. In aspects of such embodiments, the CXCR2 antagonist is administered at a dose of from 10 µg to 270 µg.

Additional embodiments of the disclosure include the pharmaceutical compositions, combinations, uses and methods set forth in above, wherein it is to be understood that each embodiment may be combined with one or more other embodiments, to the extent that such a combination is consistent with the description of the embodiments. It is further to be understood that the embodiments provided above are understood to include all embodiments, including such embodiments as result from combinations of embodiments.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., N.Y., NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol.*

Chem. 274:27371-27378; Baca et al. (1997) *J. Biol. Chem.* 272:10678-10684; Chothia et al. (1989) *Nature* 342:877-883; Foote and Winter (1992)*J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc., Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

Anti-Mouse PD-1 Antibody

In the Example below, the anti-tumor effects of a CXCR2 antagonist in combination with an anti-mouse PD1 antibody are evaluated in mouse syngeneic tumor models. Anti-tumor activity (tumor growth inhibition, tumor regression) is observed on treatment of mouse syngeneic tumors with the combination. Both mouse and human tumor infiltrating T cells express high levels of PD-1, associated with what is referred to as an "exhausted phenotype" (See Y. Jiang et al., "T-cell exhaustion in the tumor microenvironment", *Cell Death and Disease* 2015, 6, e1792). Induction of anti-tumor efficacy in mouse syngeneic tumor models following treatment with anti-mouse PD-1 antibodies provides a mechanistic rationale that treatment of cancer patients with anti-human PD-1 antibodies will induce anti-tumor efficacy (See S. Hu-Lieskovan et al., "Improved antitumor activity of immunotherapy with BRAF and MEK inhibitors in BRAF (V600E) melanoma", *Sci. Transl. Med.* 2015 Mar. 18; 7(279):279ra41; C. D. Pham et al., "Differential immune microenvironments and response to immune checkpoint blockade among molecular subtypes of murine medulloblastoma", *Clin. Cancer Res.* 2016 Feb. 1; 22(3):582-595; S. Budhu et al., "The importance of animal models in tumor immunity and immunotherapy", *Curr. Opin. Genet. Dev.* 2014, 24, 46-51). Suitable anti-mouse PD-1 antibodies that may be used include muDX400 (Merck), InVivoMAb and InVivoPlusMAb anti-mouse PD-1 clone J43 (commercially available from BioXCell as catalog number BE0033-2), InVivoMAb anti-mouse PD-1 clone 29F.1A12 (commercially available from BioXCell as catalog number BE0273), and InVivoMAb and InVivoPlusMAb anti-mouse PD-1 clone RMP1-14 (commercially available from BioXCell as catalog number BE0146).

EXAMPLES

Example 1: Anti-Tumor Efficacy of a CXCR2 Antagonist in Combination with an Anti-PD-1 Antibody in Mouse B16-F10 Melanoma Syngenic Tumor Model The combination anti-tumor efficacy of a CXCR2 antagonist and anti-mouse PD-1 antibody muDX400 was assessed in the B16-F10 melanoma tumor model, syngeneic to the C57Bl/6 strain. This experiment compared the anti-tumor response of tumor-bearing mice to treatment with one of three regimens: monotherapy with a murine anti-mouse PD-1 monoclonal antibody (Anti-PD-1), monotherapy with a CXCR2 antagonist (navarixin) and combination therapy with these two agents administered concurrently.

Tumor-bearing mice for this study were initiated by implanting $0.4 \times 10^6$ log-phase and sub-confluent B16-F10 cells on the right lower dorsal flank of 7-8 week old female C57Bl/6 mice with an average body weight of 18 grams. When the mean tumor volume in these mice reached ~70 cubic mm (50 $mm^3$-80 $mm^3$), the tumor-bearing mice were randomized to 5 treatment groups of 12 mice per group:

(1) Isotype Control+Vehicle;
(2) Isotype Control+Navarixin (bid);
(3) Anti-PD-1+Vehicle;
(4) Anti-PD-1+Navarixin (bid) and;
(5) Anti-PD-1+Navarixin (qd).

The monoclonal antibody against murine PD-1 was of the isotype IgG1. The isotype control was a mouse monoclonal antibody specific for adenoviral hexon 25 and was of the isotype IgG1. Formulations for each reagent were as follows: Isotype control: 75 mM NaCl, 10 mM sodium phosphate, 3% sucrose, pH 7.3; anti-PD-1: 20 mM sodium acetate, 7% sucrose, pH 5.5; and navarixin: 0.5% methocel with 0.25% SDS (sodium dodecyl sulfate) in sterile water. Anti-PD-1 was administered to treatment groups 2 and 4, and 5 at 10 mg/kg i.p. every 5 days for each of 4 cycles. The isotype control was administered at the same dose, schedule, and route as the anti-PD-1 antibody. Navarixin was administered at 300 mg/kg to treatment groups 3 and 4 twice daily and to treatment group 5 once daily for 15 days. The tumor volume was assessed using Vernier calipers.

Figure 3:
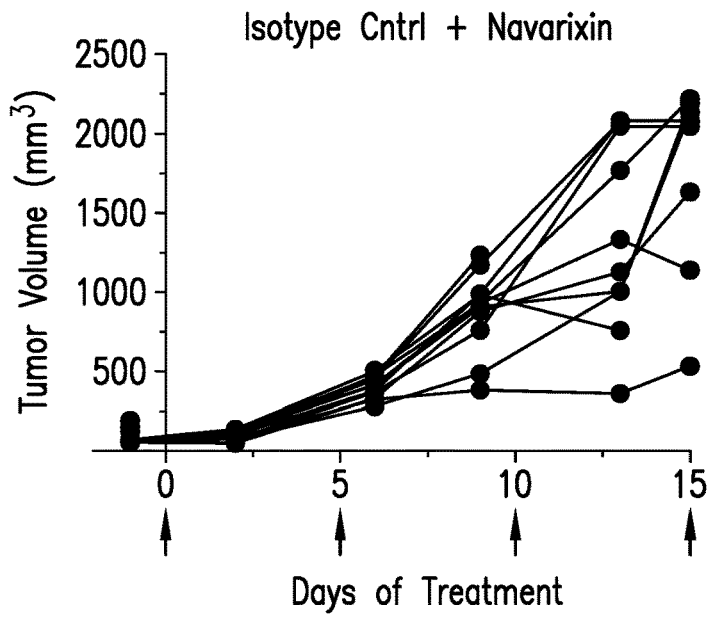
FIG. 3 shows the tumor volume vs. days of treatment in the isotype control (control IgG mouse monoclonal antibody) plus navarixin treatment group.
Figure 4:
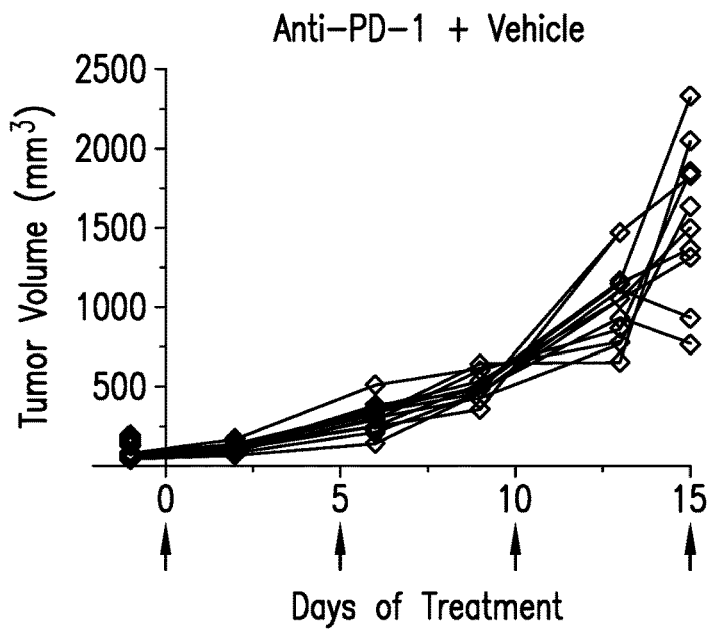
FIG. 4 shows the tumor volume vs. days of treatment in the mouse anti-PD-1 monoclonal antibody plus vehicle treatment group.
Figure 5:
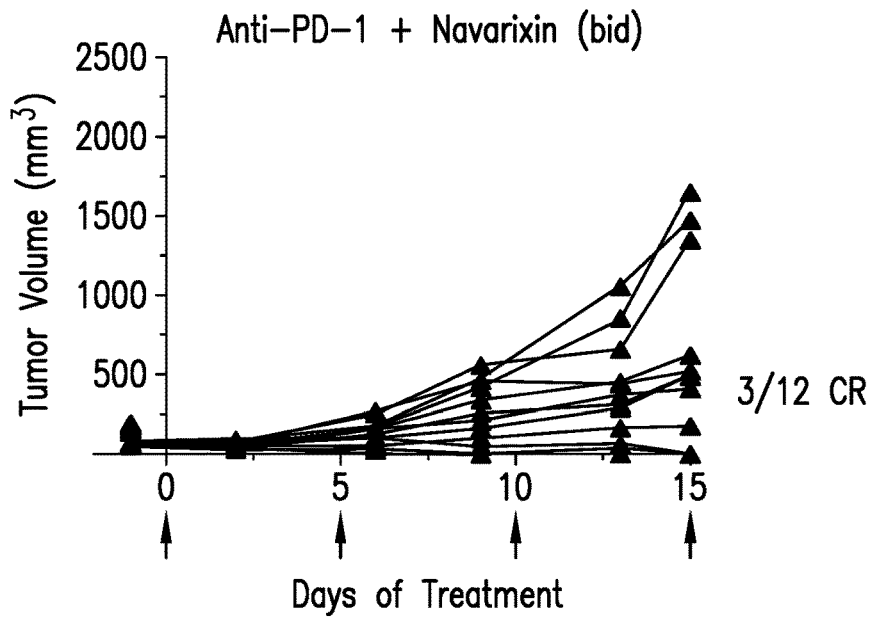
FIG. 5 shows the tumor volume vs. days of treatment in the mouse anti-PD-1 monoclonal antibody plus navarixin (bid) treatment group.
Figure 6:
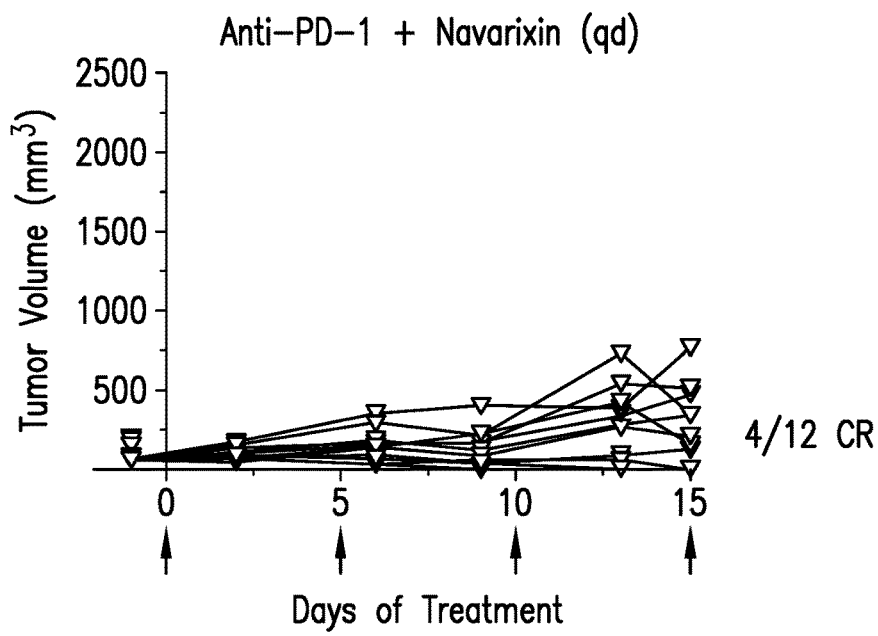
FIG. 6 shows the tumor volume vs. days of treatment in the mouse anti-PD-1 monoclonal antibody plus navarixin (qd) treatment group.

As demonstrated by the results shown in FIG. 1, the mean anti-tumor response of combination therapy with the anti- PD-1 antibody and navarixin was greater than the anti-tumor response observed with either navarixin single agent treatment administered twice daily (bid, p=0.001 two-sided p-values Gehan-Breslow nonparametric test) or anti-PD-1 (p=0.00025 two-sided values Gehan-Breslow nonparametric test) single agent treatment at Day 15. As shown in FIGS. 5 and 6, combination treatment groups demonstrated 3 out of 12 complete regressions (CR) in group 4 (FIG. 5, bid navarixin administration) and 4 out of 12 responses in group 5 (FIG. 6, qd navarixin administration) such that no measureable tumor remained. There was no significant difference between group 4 and group 5. Complete and partial regressions were not observed in the single agent treatment groups as shown in FIGS. 3 and 4. Treatment tolerability was assessed by monitoring animal body weight. There was no significant body weight loss associated with administration of single agents or combination therapy indicating that treatments were well tolerated.

Example 2: Clinical Study Evaluating Navirixin in Combination with an Anti-PD-1 Antibody in Treatment of Patients with Advanced/Metastatic Solid Tumors A Phase I clinical study will be conducted to evaluate, in part, the effects of a combination therapy, consisting of intravenous infusion of a pembrolizumab and oral administration of navarixin in participants with selected advanced or metastatic solid tumors. The study is a stratified, parallel, 2-arm (2-dose), randomized, unblended, open-label study and uses a 2-stage adaptive design based on prespecified criteria. There is no untreated/placebo comparator arm.

Participants with PD-L1 refractory non-small cell lung cancer, castration resistant prostrate cancer, or microsatellite stable colorectal cancer will be randomized into one of two dose arms. In dose Arm A, participants will be treated with 30 mg orally QD navarixin. In dose Arm B, participants will be treated with 100 mg orally QD navarixin. Participants in both Arms A and B will be treated concomitantly with pembrolizumab 200 mg intravenously every 3 weeks. Safety and tolerability will be continuously monitored throughout the study duration.

The overall design is an adaptive 2-stage design. In each arm, up to 30 participants will be enrolled in the first stage, and up to 30 participants in the second stage. In the first stage, 30 participants (with 10 per tumor type) will be enrolled in each arm (dose level). When all participants in a given arm with a given tumor type complete the first on-treatment scan at 9 weeks or when clinically indicated, a futility analysis will be conducted to determine whether that tumor type and arm will progress to Stage 2. If a tumor type passes the futility analysis in Stage 1, at least 10 participants will be enrolled with that tumor type in the second stage.

Peripheral neutrophil assessment (ANC) will occur at baseline, Day 3, and Day 8 during the first cycle for all participants. Decreased ANC counts typically return to normal in 48-96 hours following dosing cessation. Standard support for oncology patients with low ANC will be considered as appropriate.

RECIST 1.1 will be used as the primary measure for assessment of tumor response, date of disease progression, and as a basis for all protocol guidelines related to disease status (e.g., discontinuation of study treatment).

What is claimed is:

1. A method of treating prostate cancer, comprising administering:
   (a) a compound having the Formula I

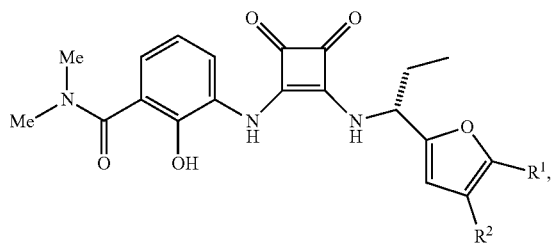

wherein $R^1$ are $R^2$ are independently H or $C_1$-$C_5$ alkyl or a pharmaceutically acceptable salt thereof; and
   (b) an anti-human PD-1 antibody or antigen binding fragment thereof to a human patient in need thereof.

2. The method of claim 1, wherein the prostate cancer is metastatic castrate-resistant prostate cancer.

3. The method of claim 1, wherein the compound of Formula I is

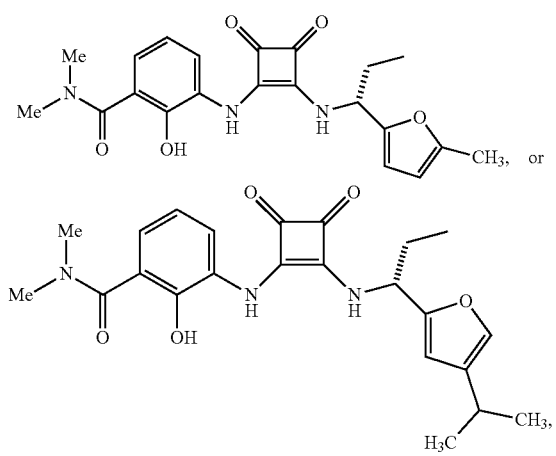

or a pharmaceutically acceptable salt thereof.

4. The method of claim 3, wherein the compound of Formula I is

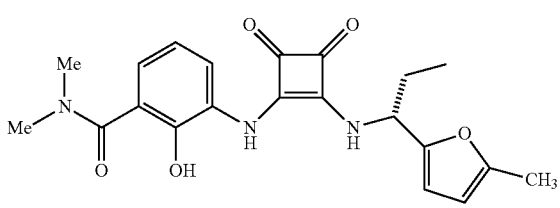 [SMILES: CC[C@@H](Nc1c(Nc2cccc(C(=O)N(C)C)c2O)c(=O)c1=O)c1ccc(C)o1]

or a pharmaceutically acceptable salt thereof.

5. The method of claim 3, wherein the compound of Formula I is

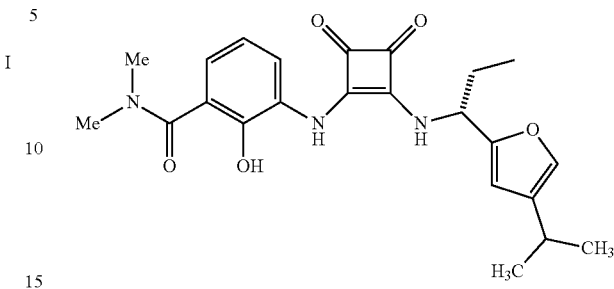

or a pharmaceutically acceptable salt thereof.

6. The method of claim 1, wherein the human patient is administered:
   (a) 200 mg or 240 mg of the anti-human PD-1 antibody or antigen binding fragment thereof and from 5 to 200 mg of the compound of Formula I or a pharmaceutically acceptable salt thereof; or
   (b) 2 mg/kg of an anti-human PD-1 antibody or antigen binding fragment thereof and from 5 to 200 mg of the compound of Formula I or a pharmaceutically acceptable salt thereof,
   wherein the anti-human PD-1 antibody or antigen binding fragment thereof is administered once every three weeks and the compound of Formula I or a pharmaceutically acceptable salt thereof is administered once daily or twice daily.

7. The method of claim 1, wherein the anti-human PD-1 antibody or antigen binding fragment thereof comprises three light chain CDRs of SEQ ID NO:1, SEQ ID NO:2 and SEQ ID NO:3 and three heavy chain CDRs of SEQ ID NO:6, SEQ ID NO:7 and SEQ ID NO:8.

8. The method of claim 1, wherein the anti-human PD-1 antibody or antigen binding fragment thereof comprises a $V_L$ region which comprises the amino acid sequence set forth in SEQ ID NO:4, and a $V_H$ region which comprises the amino acid sequence set forth in SEQ ID NO:9.

9. The method of claim 1, wherein the anti-human PD-1 antibody or antigen binding fragment thereof comprises a light chain comprising or consisting of a sequence of amino acids as set forth in SEQ ID NO:5 and a heavy chain comprising or consisting of a sequence of amino acids as set forth in SEQ ID NO:10.

10. The method of claim 1, wherein the anti-human PD-1 antibody or antigen binding fragment thereof is pembrolizumab.

11. The method of claim 1, wherein the anti-human PD-1 antibody or antigen binding fragment thereof is nivolumab.

* * * * *